United States Patent
Inoguchi

(10) Patent No.: US 9,352,975 B2
(45) Date of Patent: May 31, 2016

(54) ULTRAFINE ZINC OXIDE PARTICLE DISPERSION SOLUTION, METHOD FOR PRODUCING THE ULTRAFINE ZINC OXIDE PARTICLE DISPERSION SOLUTION, AND ZINC OXIDE THIN FILM

(75) Inventor: Masashi Inoguchi, Manchester (GB)

(73) Assignee: MURATA MANUFACTURING CO., LTD., Nagaokakyo-Shi, Kyoto-Fu (JP)

( * ) Notice: Subject to any disclaimer, the term of this patent is extended or adjusted under 35 U.S.C. 154(b) by 180 days.

(21) Appl. No.: 12/862,897

(22) Filed: Aug. 25, 2010

(65) Prior Publication Data

US 2011/0036268 A1 Feb. 17, 2011

Related U.S. Application Data

(63) Continuation-in-part of application No. PCT/JP2009/053435, filed on Feb. 25, 2009.

(30) Foreign Application Priority Data

Feb. 28, 2008 (JP) ................. 2008-047331

(51) Int. Cl.
*C09D 1/00* (2006.01)
*C01G 9/02* (2006.01)
(Continued)

(52) U.S. Cl.
CPC ............. *C01G 9/02* (2013.01); *A61K 8/0241* (2013.01); *A61K 8/27* (2013.01); *A61K 8/39* (2013.01);
(Continued)

(58) Field of Classification Search
CPC . H01L 21/31691; H01L 28/55; C23C 16/448; C23C 18/1216; C23C 16/40; C23C 22/74; B82Y 30/00; C09D 163/00; C03C 17/22
See application file for complete search history.

(56) References Cited

U.S. PATENT DOCUMENTS 5,990,373 A * 11/1999 Klabunde ................... 588/313
2008/0032134 A1* 2/2008 Whiteford et al. ........ 428/402.24
(Continued)

FOREIGN PATENT DOCUMENTS

JP 02-059425 A 2/1990
JP 2004-075464 A 3/2004
(Continued)

OTHER PUBLICATIONS

Chemical Book, p. 1-1, 2012.*
(Continued)

*Primary Examiner* — Melissa Swain
(74) *Attorney, Agent, or Firm* — Arent Fox LLP

(57) ABSTRACT

In an ultrafine ZnO particle dispersion, ultrafine ZnO particles are dispersed and float in a hydrophobic solvent while being surrounded by a surfactant composed of a primary surfactants such as polyoxyethylene nonylphenyl ether, and a secondary surfactant such as 1-octanol. The ultrafine ZnO particles have an average particle diameter $D_{50}$ of 10 nm or less and a ratio of the standard deviation σ to the average particle diameter $D_{50}$, $σ/D_{50}$, of 0.2 or less. The average particle diameter $D_{50}$ of the ultrafine ZnO particles can be controlled by changing the side chain length of the hydrophilic group of the primary surfactant. A ZnO thin film produced by using this dispersion solution has a ratio of a maximum emission intensity in a visible region to a maximum emission intensity in a ultraviolet region, P1/P2, of 0.2 or less. Thereby, an ultrafine ZnO particle dispersion solution in which ultrafine ZnO particles having a very narrow width of particle size distribution and being in nanometer level with an average particle diameter of 10 nm or less are present in a monodispersed state, and a ZnO thin film produced by using this are realized.

15 Claims, 25 Drawing Sheets

(51) Int. Cl.
- *A61K 8/02* (2006.01)
- *A61K 8/27* (2006.01)
- *A61K 8/39* (2006.01)
- *A61K 9/00* (2006.01)
- *A61K 9/10* (2006.01)
- *A61K 9/16* (2006.01)
- *B01J 13/02* (2006.01)
- *B82Y 30/00* (2011.01)

(52) U.S. Cl.
CPC .............. *A61K 9/0014* (2013.01); *A61K 9/10* (2013.01); *A61K 9/1688* (2013.01); *B01J 13/02* (2013.01); *B82Y 30/00* (2013.01); *A61K 2800/412* (2013.01); *A61K 2800/413* (2013.01); *A61K 2800/612* (2013.01); *C01P 2002/72* (2013.01); *C01P 2002/85* (2013.01); *C01P 2004/03* (2013.01); *C01P 2004/04* (2013.01); *C01P 2004/52* (2013.01); *C01P 2004/64* (2013.01)

(56) References Cited

U.S. PATENT DOCUMENTS

| 2009/0280327 A1* | 11/2009 | Ying et al. ............... 428/405 |
| 2010/0117503 A1 | 5/2010 | Mizuno et al. |
| 2010/0144945 A1* | 6/2010 | Nakazawa et al. ........ 524/417 |

FOREIGN PATENT DOCUMENTS

| JP | 2004-182483 A | 7/2004 |
| JP | 2004182483 | * 7/2004 |
| JP | 2004-300013 A | 10/2004 |
| JP | 2007-070188 A | 3/2007 |
| JP | 2007-204354 A | 8/2007 |

OTHER PUBLICATIONS

Eric A. Meulenkamp, "Synthesis and Growth of ZnO Nanoparticles", J. Phys. Chem. B 1998, 102, 5566-5572.*

Ch. Beck, et al.; "Size-controlled synthesis of nanocrystalline $BaTiO_3$ by a sol-gel type hydrolysis in microemulsion-provided nanoreactors"; Journal of Materials Research, vol. 13, No. 11, Nov. 1998, pp. 3174-3180.

Y. Yamashita, et al.; "Dielectric Properties of $BaTiO_3$ Thin Films Derived from Clear Emulsion of Well-Dispersed Nanosized $BaTiO_3$ Particles"; Japanese Journal of Applied Physics, vol. 43, No. 9B, 2004, pp. 6521-6524.

International Search Report, Form PCT/ISA/210, mailed Jun. 16, 2009 (Japanese language).

Koran, A.R., et al.; "Nucleation and Growth of CdSe on ZnS Quantum Crystallite Seeds, and Vice Versa, in Inverse Micelle Media"; J. Am. Chem. Society; vol. 112, No. 4, 1990; pp. 1327-1332.

"Thin-Film Coating Technique by Sol-Gel Method"; Technical Information Institute Co., Ltd.; Sections 3 and 4 translated from Japanese,1994; pp. 98-106.

* cited by examiner

Fig. 5
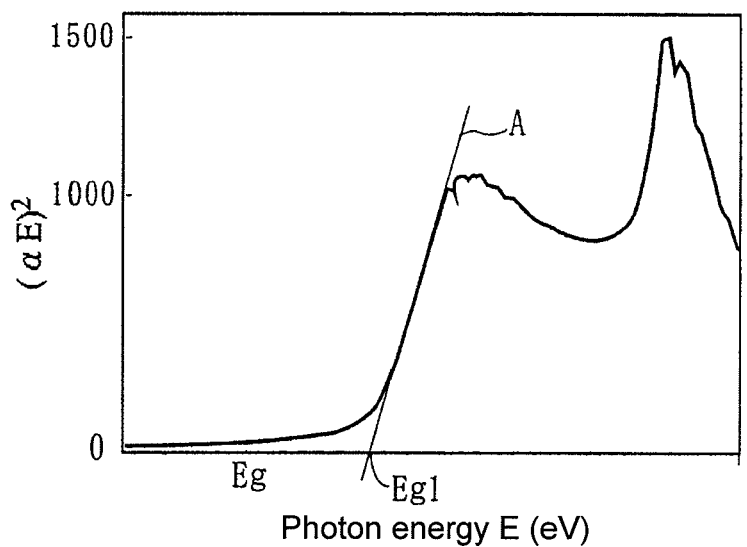
Fig. 6(a)  Fig. 6(b)
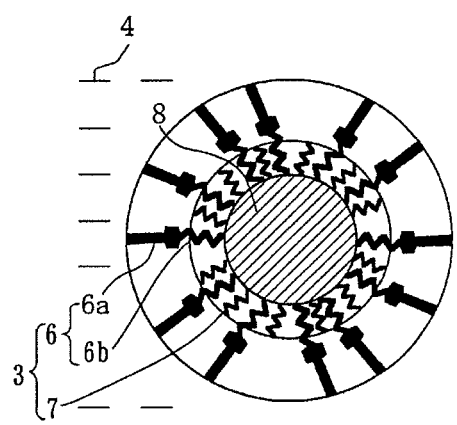
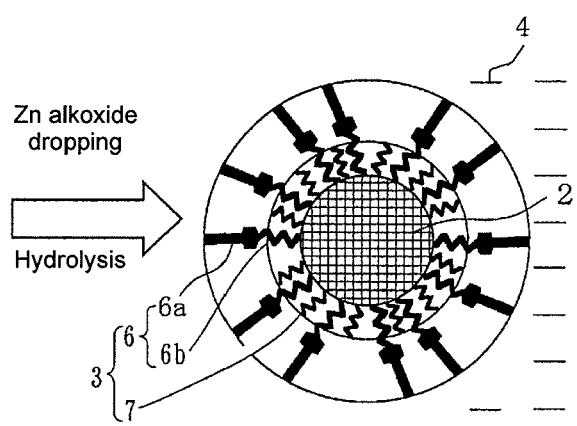

10nm

10nm

10nm

10nm

2nm

100nm

ULTRAFINE ZINC OXIDE PARTICLE DISPERSION SOLUTION, METHOD FOR PRODUCING THE ULTRAFINE ZINC OXIDE PARTICLE DISPERSION SOLUTION, AND ZINC OXIDE THIN FILM

This is a continuation-in-part of application serial no. PCT/JP2009/053435, filed Feb. 25, 2009, which is hereby incorporated herein by reference.

TECHNICAL FIELD

The present invention relates to an ultrafine zinc oxide particle dispersion, a method for producing the ultrafine zinc oxide particle dispersion, and a zinc oxide thin film, and particularly to an ultrafine zinc oxide particle dispersion produced by using a water-in-oil type microemulsion, a method for producing the same, and a zinc oxide thin film produced by using the ultrafine zinc oxide particle dispersion.

BACKGROUND ART

Zinc oxide (henceforth referred to as "ZnO") is widely used in various fields because it is an inexpensive, nontoxic material and it has various properties such as a semiconductor characteristic, an electrical conductivity and a piezoelectric property.

On the other hand, theories, technologies and devices of nanometer level have recently been under active study, and the development of ultrafine particle materials and ultrafine particle thin films has been demanded in many technical fields.

In particular, ultrafine particles of the ZnO are used for cosmetics, e.g., a sunscreen agent, and medical and pharmaceutical applications, e.g., a drug carrier, and ZnO is a direct transition type semiconductor having excellent luminous efficiency. Therefore, ZnO has been studied as a photocatalyst, in a UV shielding paint, and in emissive materials such as UV laser/LED, and its application to a gas sensor, an optical sensor, semiconductor conduction type control, an electrode material for dye-sensitized solar cells, and the like, has been studied actively.

Such ultrafine ZnO particles have conventionally been produced by various methods, such as a solid phase process, a gas phase process and a liquid phase process.

As a method for producing ultrafine ZnO particles by a solid phase process, known is a pulverization process in which large particles are mechanically pulverized to form fine particles.

However, although this pulverization process is a method suitable for producing a fine particle raw material at a low cost, impurities are easily incorporated into ZnO and it is difficult to obtain ZnO particles with a high purity because of the use of a pulverizing medium. Moreover, the pulverization process has a limit in the degree of particle size reduction because ZnO having a relatively large particle diameter is pulverized, and it is difficult to obtain ultrafine ZnO particles, that is, particles of nanometer level, and having a uniform particle diameter (as they have a wide particle size distribution).

As a method of producing an ultrafine ZnO particle thin film by a gas phase process, known are various methods such as a sputtering process, a molecular beam epitaxy process, a chemical vapor growth process and a laser ablation process.

However, these gas phase processes need an expensive equipment environment such as ultra-high vacuum, high voltage, high heat and a laser, and moreover, there is a need to control the environment strictly.

The liquid phase process can produce ultrafine ZnO particles in a comparatively simple environment compared with the gas phase processes. As a method for producing ultrafine ZnO particles by a liquid phase process, there have conventionally been known a hydrothermal synthesis process, a sol-gel process, a microemulsion process, and the like.

However, the hydrothermal synthesis process needs a large-scale apparatus because a raw material powder is dissolved by using water as a solvent under a high temperature and a high pressure in an autoclave.

Although the sol-gel process can provide ultrafine ZnO particles by hydrolyzing a Zn alkoxide, it is necessary to carry out a very slow hydrolysis reaction which requires several days.

Moreover, since dissolved raw materials in the hydrothermal synthesis process or the sol-gel process are reacted in a continuous phase, the particle size distribution tends to become wide, and agglomeration and sedimentation of particles easily occur. Therefore, it is difficult to obtain ultrafine ZnO particles with a uniform quality on the nanometer level. Furthermore, hydroxyl groups or hydrocarbons which are present in a solution may be incorporated into the ZnO particles, and impurities are easily incorporated into ZnO particles, so that the resulting ZnO thin film may become amorphous.

If the ultrafine particles have a size of 10 nm or less in such liquid phase processes, the particles easily agglomerate and, therefore, it is difficult to obtain ultrafine ZnO particles in a monodispersed state.

On the other hand, a microemulsion process is a process configured to obtain ultrafine particles by producing a water-in-oil (henceforth referred to as "W/O") type microemulsion by mixing a hydrophobic solvent, a surfactant and water, then pouring raw materials into the microemulsion, and causing a hydrolysis reaction to take place. In this microemulsion process, it is conceivable that a high-purity ultrafine particle material having a relatively narrow particle size distribution can be obtained because the ultrafine particles are formed through a hydrolysis reaction carried out in water droplets surrounded by a surfactant.

In patent document 1, there is proposed ultrafine ZnO particles produced by adding a Zn alkoxide or a Zn alkoxyalkoxide to a W/O type microemulsion phase of a surfactant-water-nonpolar organic liquid type or a surfactant-water-alkanol-nonpolar organic liquid type, and performing a hydrolysis reaction.

In the patent document 1, nonylphenol ethoxylate ($C_9H_{19}$—$C_6H_4$—$O(CH_2CH_2O)_6H$) (Terginol NP-6) is used as a surfactant, cyclohexane is used as a nonpolar organic liquid, and Zn di-n-butoxide is used as a Zn alkoxide. After ammonia water is solubilized in the surfactant and cyclohexane by adding it so that the amount of water is about 2 to 8 times the amount of the surfactant, Zn di-n-butoxide is added and stirred, and thereby ultrafine ZnO particles having an average particle diameter of 300 Å (30 nm) are obtained.

Moreover, patent document 2, which relates to mixed metal oxide ultrafine particles such as barium titanate ($BaTiO_3$), proposes an ultrafine metal oxide particle dispersion solution produced by a hydrolysis reaction of a raw material in a microemulsion containing a dispersing medium, which is a hydrophobic liquid, water and a surfactant, wherein the raw material is composed of a mixed metal alkoxide solution hybridized by mixing a plurality of metal alkoxides in alcohol, and the amount of water contained in the microemulsion is 0.95 to 3 times the amount of water necessary for the hydrolysis of the raw material.

A water-in-oil type microemulsion solution is obtained in the patent document 2 using cyclohexane as a hydrophobic liquid, para-nonylphenol ethoxylate ((p-$C_9H_{19}$)—$C_6H_4$—O—$(CH_2CH_2O)_{10}CH_2CH_2OH$) (Terginol NP-10) as a surfactant, and 1-octanol as a secondary surfactant. A Ba—Ti mixed alkoxide solution is supplied to the microemulsion solution so that the amount of water in the microemulsion solution is 0.95 to 3 times the amount of water necessary for the hydrolysis of the Ba—Ti mixed alkoxide, and thereby an ultrafine $BaTiO_3$ particle dispersion in which $BaTiO_3$ ultrafine particles having an average particle diameter of 10 nm or less are dispersed is obtained.

Patent document 1: JP 2-59425 A (claims, from line 1 to line 6 on the lower right-hand section in page 4, and FIG. 1)

Patent document 2: JP 2004-300013 A

DISCLOSURE OF THE INVENTION

Problem to be Solved by the Invention

However, patent document 1, in which a hydrolysis reaction is caused in a W/O type microemulsion solution and thereby ultrafine ZnO particles are obtained, had a problem in that the average particle diameter of the ultrafine ZnO particles was as large as 30 nm and it was impossible to obtain ultrafine ZnO particles of 10 nm or less. It is conceivable that since the amount of water to the surfactant was as large as about 2 to 8 times, the particle diameter of water drops dispersed in the solution was also large, so that the particle diameter of ultrafine ZnO particles resulting from hydrolysis became large.

Furthermore, although patent document 1 has a disclosure that indicates ZnO having a sharp particle size distribution can be obtained, a quantitative evaluation was not done and what the actual particle size distribution is unknown.

In patent document 2, a mixed metal alkoxide is dropped into a microemulsion solution, as mentioned above and thereby ultrafine particles of a metal mixed oxide such as $BaTiO_3$ is obtained.

However, it is difficult to apply the technique of patent document 2 directly to the production of ultrafine ZnO particles, which has different chemical properties, for the following reasons.

In order to obtain ultrafine ZnO particles having an average particle diameter of 10 nm or less, it is necessary to inhibit the amount of water contained in the microemulsion solution from increasing during the reaction, and it is preferable for this purpose to use an anhydrous Zn alkoxide.

Although Ba alkoxide and Ti alkoxide, which are disclosed in patent document 2, dissolve in an alcoholic solution easily, Zn alkoxide hardly dissolves in an alcoholic solution. Therefore, even if the technique of patent document 2 is applied, it is difficult to obtain a desired ultrafine ZnO particle dispersion.

The present invention has been devised in view of such a situation, and an object thereof is to provide an ultrafine ZnO particle dispersion in which ultrafine ZnO particles having a very narrow width of particle size distribution and being in nanometer level (an average particle diameter of 10 nm or less) are present in a monodispersed state, a method for producing the ultrafine ZnO particle dispersion, and a ZnO thin film.

Means for Solving the Problem

By hydrolyzing a ZnO compound in water drops dispersed and floating in a W/O type microemulsion, ultrafine ZnO particles having a particle diameter according to the diameter of the water drops can be formed, and therefore it is conceivable that a dispersion in which desirably ultrafine ZnO particles are dispersed can be obtained if the water drops have an ultrafine diameter.

Therefore, the use of a nonahydrate such as a Zn alkoxide is desired as the ZnO compound rather than hydrates such as Zn acetate which will cause an increase in the amount of moisture; however, Zn alkoxide is known to hardly dissolve in alcohol, as described above.

The present inventor studied earnestly and found that by using an aminoalcohol such as monoethanolamine together with the Zn alkoxide, it was possible to dissolve the Zn alkoxide in alcohol and the aminoalcohol does not dissolve in a hydrophobic solvent.

Specifically, he obtained findings that by using a Zn alkoxide together with an aminoalcohol and dissolving it in an alcohol to produce a Zn alkoxide solution, and then adding the Zn alkoxide solution into a W/O type microemulsion, it is possible to hydrolyze the Zn alkoxide efficiently by using ultrafine water drops as a reaction field without allowing excess moisture to enter into the water drops, and thereby ultrafine ZnO particles having an average particle diameter $D_{50}$ of 10 nm or less and a ratio of the standard deviation $\sigma$ to the average particle diameter $D_{50}$, $\sigma/D_{50}$, of 0.2 or less can be obtained.

The present invention was made on the basis of such findings, and the ultrafine ZnO particle dispersion (henceforth referred to as a "ZnO dispersion") according to the present invention is characterized in that ultrafine ZnO particles having an average particle diameter $D_{50}$ of 10 nm or less and a ratio of the standard deviation $\sigma$ to the average particle diameter $D_{50}$, $\sigma/D_{50}$, of 0.2 or less are dispersed in a hydrophobic solvent with individual particles surrounded by a surfactant.

Moreover, the ZnO dispersion of the present invention is characterized in that the ultrafine ZnO particles preferably have an average particle diameter $D_{50}$ of 5 nm or less.

Moreover, the ZnO dispersion of the present invention is characterized in that the ultrafine ZnO particles are formed by a hydrolysis reaction of a Zn alkoxide in a W/O type microemulsion in which the surfactant and water are dispersed in a hydrophobic solvent.

Furthermore, the ZnO dispersion of the present invention is characterized in that the Zn alkoxide is preferably diethoxy Zn.

Moreover, repeating earnest studies by using polyoxyethylene nonylphenyl ether (henceforth referred to as "NPE (n)") as a nonionic surfactant, the present inventor found that the average particle diameter of ultrafine ZnO particles could be controlled by changing the side chain length n of the hydrophilic group of the surfactant.

Furthermore, he also found that it was possible to efficiently confine the Zn alkoxide within a surfactant and thereby to promote a desired hydrolysis reaction by using the NPE(n) as a primary surfactant and a medium chain alcohol as a secondary surfactant.

The dispersion solution of the present invention is characterized in that the surfactant includes a primary surfactant and a secondary surfactant and the average particle diameter $D_{50}$ of the ultrafine ZnO particles is controlled by a side chain length n of a hydrophilic group of the primary surfactant.

Moreover, the ZnO dispersion of the present invention is characterized preferably in that the primary surfactant is NPE (n) represented by the chemical formula:

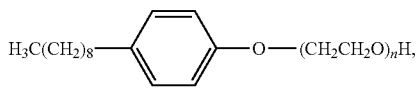

wherein n is a positive integer, preferably 1 to 20)

and that the secondary surfactant is a medium chain alcohol, preferably an alkanol represented by a chemical formula $C_mH_{2m+1}OH$ (wherein m is an integer of 4 to 10).

The method for producing a ZnO dispersion according to the present invention is characterized by including an emulsion solution preparation step including mixing hydrophobic solvent, surfactant and water to prepare a W/O type microemulsion in which water drops are dispersed in an oil, a Zn alkoxide solution preparation step including mixing and stirring a Zn alkoxide and an aminoalcohol in an alcohol to prepare a Zn alkoxide solution, and a ZnO formation step including combining the Zn alkoxide solution with the microemulsion and causing a hydrolysis reaction to form ultrafine ZnO particles having an average particle diameter $D_{50}$ of 10 nm or less and a ratio of a standard deviation σ to the average particle diameter $D_{50}$, $σ/D_{50}$, of 0.2 or less.

The method for producing a dispersion solution of the present invention is further characterized in that the molar amount of the aminoalcohol added to the alcoholic solution is at least the same molar amount as the Zn alkoxide added to the alcoholic solution.

Furthermore, the method for producing a dispersion of the present invention is preferably characterized by using diethoxy Zn as the Zn alkoxide, using monoethanolamine as aminoalcohol, and using ethanol as the alcohol.

Moreover, the method for producing a dispersion solution of the present invention is preferably characterized in that the surfactant includes a primary surfactant and a secondary surfactant, and is characterized by using NPE(n) represented by the chemical formula:

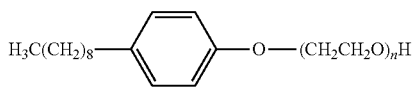

(wherein n is a positive integer of 1 to 20)
as the primary surfactant and using a medium chain alcohol represented by a chemical formula $C_mH_{2m+1}OH$ (wherein m is an integer of 4 to 10) as the secondary surfactant.

A the ZnO thin film according to the present invention is characterized by being produced using the dispersion solution.

A ZnO thin film of the present invention is characterized in that the ratio of a maximum emission intensity P1 in a visible range to the maximum emission intensity P2 in an ultraviolet range, P1/P2, is 0.2 or less.

The ZnO thin film of the present invention can be produced by applying the dispersion onto a substrate and subjecting it to heat treatment.

Furthermore, that the average particle diameter of the ZnO thin film of the present invention can be controlled by the treatment temperature of the heat treatment.

Effect of the Invention

As to the dispersion solution of the present invention, since ultrafine ZnO particles having an average particle diameter $D_{50}$ of 10 nm or less (preferably 5 nm or less) and having a ratio of the standard deviation σ to the average particle diameter $D_{50}$, $σ/D_{50}$, of 0.2 or less are dispersed in a hydrophobic solvent with individual particles surrounded by a surfactant, it is possible to obtain a dispersion solution of ultrafine ZnO particles which are of nanometer level in particle diameter, have a very narrow particle size distribution and are dispersed in a hydrophobic solvent in a monodispersed state.

Since the ultrafine ZnO particles are formed by a hydrolysis reaction of a Zn alkoxide such as diethoxy Zn in a W/O type microemulsion in which the surfactant and water are dispersed in a hydrophobic solvent, it is possible to efficiently form ultrafine ZnO particles with a particle diameter according to a very small water drop diameter.

Since the surfactant includes a primary surfactant such as NPE(n), and a secondary surfactant such as a medium chain alcohol, and the average particle diameter $D_{50}$ of the ultrafine ZnO particles is controlled by the side chain length n of a hydrophilic group of the primary surfactant, the average particle diameter $D_{50}$ of ultrafine ZnO particles can be easily adjusted by properly choosing a primary surfactant differing in side chain length n, and it is possible to easily obtain a dispersion solution in which ultrafine ZnO particles having an average particle diameter $D_{50}$ desired for an intended application are monodispersed.

Moreover, the use of the secondary surfactant in addition to the primary surfactant makes it possible to allow water drops to exist while being stabilized during this microemulsion preparation process of a.

Since the method of for producing a dispersion solution of the present invention includes an emulsion preparation step including mixing a hydrophobic solvent, a surfactant such as NPE(n) and a medium chain alcohol, and water to prepare a W/O type microemulsion in which water drops are dispersed in an oil, a Zn alkoxide solution preparation step including mixing and stirring a Zn alkoxide such as diethoxy Zn, and an aminoalcohol such as monoethanolamine in an alcoholic medium such as ethanol to prepare a Zn alkoxide solution, and a ZnO formation step including introducing the Zn alkoxide solution into the microemulsion solution and causing a hydrolysis reaction to form the ultrafine ZnO particles having an average particle diameter $D_{50}$ of 10 nm or less and having a ratio of the standard deviation σ to the average particle diameter $D_{50}$, $σ/D_{50}$, of 0.2 or less, it becomes possible to form ultrafine ZnO particles having a particle diameter according to the diameter of water drops dispersed in the microemulsion solution without causing the increase in the amount of water, and it is possible to produce a ZnO dispersion which is ultrafine, narrow in particle size distribution, homogeneous, and surrounded stably by a surfactant.

Moreover, since the added molar amount of the aminoalcohol to the alcoholic medium is at least the same molar amount as the added molar amount of the Zn alkoxide to the alcoholic solution, the Zn alkoxide is dissolved in the alcoholic solution completely, so that no insoluble Zn alkoxide in the alcoholic solution remains.

Since the ZnO thin film of the present invention is produced by using the dispersion solution, crystallized ultrafine ZnO particles are used, so that it is possible to obtain a ZnO thin film constituted of single crystal ultrafine ZnO particles.

Since the ZnO thin film is characterized by a ratio of a maximum emission intensity P1 in a visible range to a maximum emission intensity P2 in an ultraviolet range, P1/P2, is 0.2 or less, it is possible to obtain a ZnO thin film which exhibits weak visible emission caused by the defect level such as oxygen defect, and exhibits strong ultraviolet emission caused by interband transition or exciton recombination. Namely, it is possible to obtain a ZnO thin film which contains few defects, has a high crystallinity, exhibits strong ultraviolet emission and is excellent in visible light permeability.

Moreover, since the ZnO thin film is obtained by applying the ZnO dispersion onto a substrate and subjecting it to heat treatment, the ZnO particles grow during the heat treatment and, it is therefore possible to produce a high-quality ZnO thin film which is free of defects such as cracks.

Furthermore, since the average particle diameter of the ZnO thin film is controlled by the temperature of the heat treatment, it is possible to obtain a ZnO thin film with the quality desired according to its intended application only by changing the temperature of the heat treatment of the same ultrafine ZnO particle dispersion, and it becomes possible to obtain a ZnO thin film useful for the preparation of an ultraviolet emission device or a quantum device, particularly by forming a film at a low temperature.

BRIEF EXPLANATION OF DRAWINGS

FIG. 5 is a diagram showing one example of the E-$(\alpha E)^2$ characteristic diagram of the dispersion solution of the present invention.

FIGS. 6(a) and 6(b) are a schematic diagrams for explaining the method for producing a dispersion solution according to the present invention.

DESCRIPTION OF REFERENCE SYMBOLS

Figure 1:
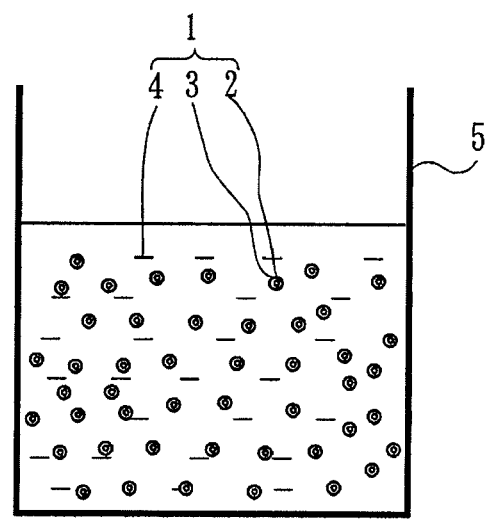
FIG. 1 is a front view schematically showing one embodiment of the dispersion solution according to the present invention.

2 Ultrafine ZnO particle
3 Surfactant
4 Hydrophobic solvent
6 Primary surfactant (NPE(n))
6a Hydrophilic group
7 Secondary surfactant
8 Water drop
9 Substrate
10 ZnO thin Film

BEST MODE FOR CARRYING OUT THE INVENTION

Next, the embodiments of the present invention will be explained in detail with reference to the drawings.

FIG. 1 is a front view in which a ZnO dispersion as one embodiment of the present invention shown schematically. In this ZnO dispersion 1, the ultrafine ZnO particles 2 are dispersed and float in a hydrophobic solvent 4 while being surrounded by a surfactant 3. Such a ZnO dispersion 1 is contained in a container 5.

Figure 2:
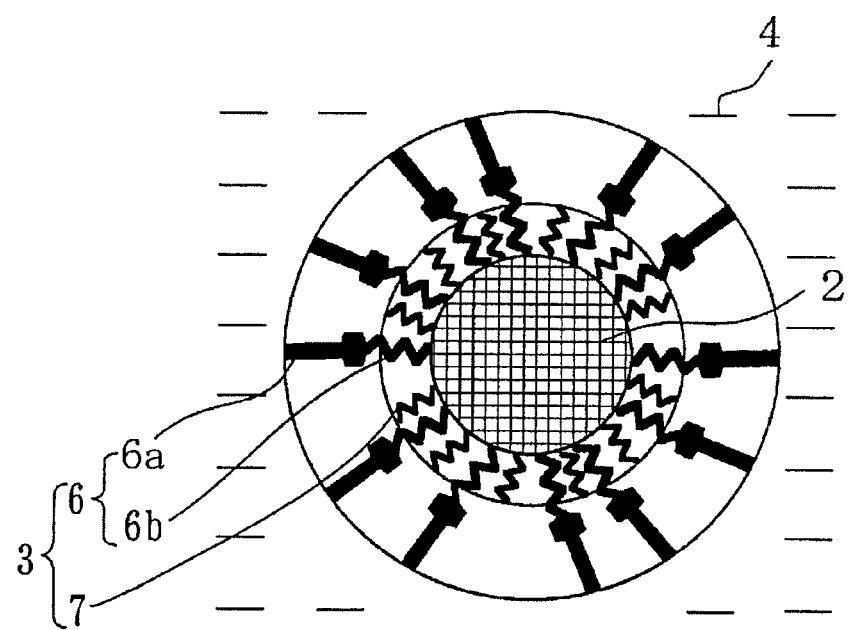
FIG. 2 is an enlarged view of a principal part of FIG. 1.

Specifically, the surfactant 3 is composed of primary surfactant 6 and secondary surfactant 7 as shown in FIG. 2.

The primary surfactant 6 has a hydrophobic group 6a and a hydrophilic group 6b; the hydrophobic group 6a is adsorbed by the hydrophobic solvent 4 and the hydrophilic group 6b is adsorbed by the ultrafine ZnO particles 2.

It is preferable to use, as the primary surfactant 3, a polyoxyethylene alkyl phenyl ether (APE (n)) whose hydrophilicity is a function of the $(CH_2CH_2O)_n$ moiety thereof, especially, NPE (n) represented by chemical formula (A):

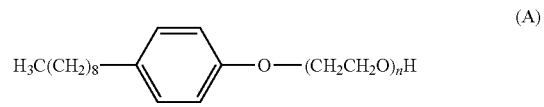
(A)

(wherein n is a positive integer which is preferably 1 to 20).

It becomes possible to control the average particle diameter $D_{50}$ of resulting ultrafine ZnO particles by changing the side chain length n of NPE (n). Namely, there is a tendency that when the length of a side chain length n becomes longer, the average particle diameter $D_{50}$ of ultrafine ZnO particles becomes smaller in comparison to when the length of the side chain length n is short. This is considered because when the length of a side chain length n becomes longer, the hydrophilic group also becomes longer and therefore, the adsorption power to water drops which contributes to the formation of ultrafine ZnO particles becomes stronger, so that the diameter of water drops becomes smaller and, as a result, the average particle diameter $D_{50}$ of the resulting ultrafine ZnO particles 2 also becomes smaller. In general, n will preferably be in the range of 1 to 20, although it could be larger.

Thus, it becomes possible to control the average particle diameter $D_{50}$ of ultrafine ZnO particles 2 by using the difference in the side chain length n of NPE (n). Therefore, it becomes possible to control the average particle diameter $D_{50}$ of ultrafine ZnO particles only by choosing NPE (n) differing in the side chain length n.

The secondary surfactant 7 has an effect to enter the internal part of a hydrophilic group 6b of a primary surfactant 6 to reduce the interfacial energy with water and to reduce the steric hindrance by the side chain length n of the hydrophilic group 6b at the time of the microemulsion preparation mentioned later, and thereby contributes the stabilization of water droplets.

When ultrafine ZnO particles 2 are formed, the secondary surfactant is adsorbed to the ultrafine ZnO particles 2 with the hydrophilic group 6b of the primary surfactant 6 while surrounding the ultrafine ZnO particles 2, so that it contributes to disperse the ultrafine ZnO particles 2 with stability in the hydrophobic solvent 4.

As such a secondary surfactant 7, a medium chain alcohol represented by a chemical formula $C_mH_{2m+1}OH$ (wherein m is from 4 to 10), e.g., 1-octanol ($C_8H_{17}OH$), can be used. Although the effect of the number of carbon atoms m depends on the length of the side chain length n of the hydrophilic group 6b of a primary surfactant 6, the hydrophilicity increases excessively if the number of carbon atoms m is less than 4, so that the secondary surfactant 7 may dissolve in water drops during microemulsion preparation and, as a result, the secondary surfactant 7 may fail to exist only in an interface between the primary surfactant 6 and water. On the other hand, that the number of carbon atoms m exceeds 10 is undesirable because the hydrophobicity may become excessively large or the steric hindrance may become large.

As the hydrophobic solvent 4, nonpolar hydrocarbons such as cyclohexane, hexane, cyclopentane, benzene, and octane; ethers such as diethyl ether and isopropyl ether; petroleum hydrocarbons such as kerosene; and the like, can be used.

The ultrafine ZnO particles 2 have been formed so that the average particle diameter $D_{50}$ may be 10 nm or less, preferably 5 nm or less, and the ratio of the standard deviation $\sigma$ represented by the equation (1) given below and the average particle diameter $D_{50}$, $\sigma/D_{50}$, may be 0.2 or less.

$$\sigma = \sqrt{\frac{\sum_{i=1}^{N}(D_s - D_{50})^2}{N}} \tag{1}$$

Here, N is the total number of the ultrafine ZnO particles 2, and $D_i$ is the measured particle diameter of an individual ultrafine ZnO particle 2.

Thereby, it is possible to obtain a ZnO dispersion 1 in which ultrafine single-crystal ZnO particles 2 are extremely small in particle diameter and extremely narrow in particle size distribution width are dispersed and float in a monodispersed state in a hydrophobic solvent 4 without agglomerating.

In this embodiment, since the ultrafine ZnO particles 2 having an average particle diameter $D_{50}$ of 10 nm or less (preferably 5 nm or less) and having a ratio $\sigma/D_{50}$ of 0.2 or less are dispersed in a hydrophobic solvent 4 with individual particles surrounded by a surfactant, it is possible to obtain a ZnO dispersion 1 in which ultrafine ZnO particles which are extremely small, are extremely narrow in particle size distribution width, are homogeneous and are in the form of single crystals are dispersed in a monodispersed state.

Although the fact that ultrafine ZnO particles having an average particle diameter $D_{50}$ of 10 nm or less are dispersed in a solution can be confirmed by directly observing them with a transmission electron microscope (henceforth "TEM") or by a selected area electron diffraction image, it can be examined easily also by measuring the transmission spectrum and extinction spectrum.

Figure 3:
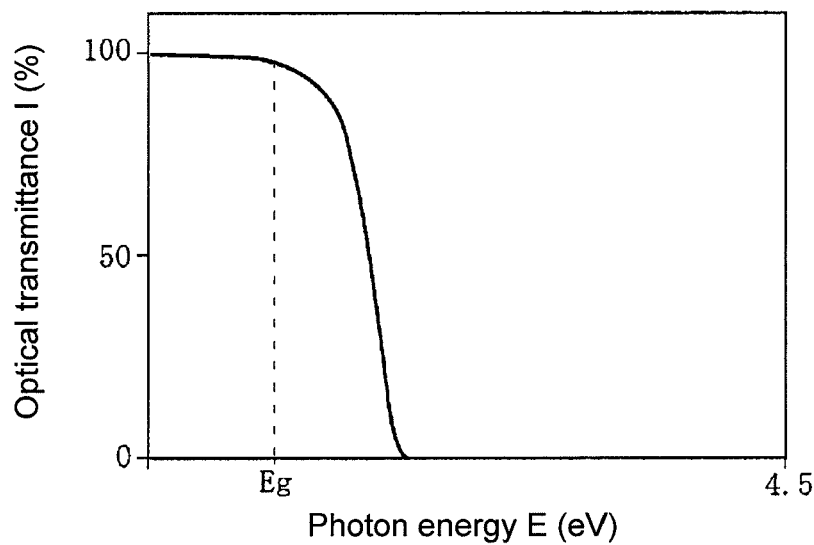
FIG. 3 is a diagram showing one example of the transmission spectrum of the dispersion solution of the present invention.

FIG. 3 is a diagram showing the transmission spectrum of the dispersion solution 1, wherein the ordinate indicates the optical transmittance I (%) and the abscissa indicates the photon energy E (eV).

It is known that the bandgap energy Eg of bulk ZnO is about 3.3 eV. When there are ultrafine ZnO particles 2 in a dispersion solution 1, although the optical transmittance I is about 100% in such an energy area that the photon energy E is equal to or smaller than the bandgap energy Eg as shown in FIG. 3, the optical transmittance I decreases rapidly and the solution becomes completely opaque to light in an energy area greater than the bandgap energy Eg.

Therefore, whether ultrafine ZnO particles are dispersed in the ZnO dispersion 1 or not can be examined by measuring the transmission spectrum of the solution.

Similarly, whether ultrafine ZnO particles 2 are dispersed in the ZnO dispersion 1 or not can be examined also by measuring the absorption spectrum of the dispersion solution 1. Whether ultrafine ZnO particles 2 are micronized to such a nanometer level that the average particle diameter $D_{50}$ is 10 nm or less also can be examined simultaneously.

Figure 4:
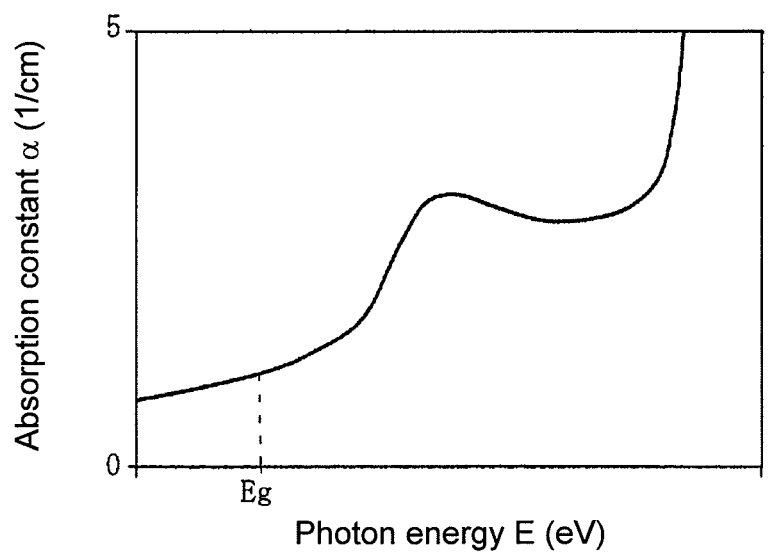
FIG. 4 is a diagram showing one example of the absorption spectrum of the dispersion solution of the present invention.

FIG. 4 is a diagram showing the absorption spectrum of the ZnO dispersion 1, wherein the ordinate indicates the absorption constant (1/cm) and the abscissa indicates the photon energy E (eV).

When the absorption constant $\alpha$ of the ZnO dispersion 1 is measured, the absorption constant $\alpha$ increases rapidly in such an energy area that the photon energy E exceeds the bandgap energy Eg of bulk ZnO (=3.3 eV) as shown in FIG. 4. This shows that ultrafine ZnO particles 2 are dispersed at least in the dispersion.

Therefore, whether ultrafine ZnO particles are dispersed in a dispersion solution 1 or not can be examined also by measuring the absorption spectrum of the solution.

Moreover, from an $E$-$(\alpha E)^2$ characteristic diagram to be obtained from the absorption spectrum, it is possible to examine whether ultrafine ZnO particles are micronized to such a nanometer level that the average particle diameter $D_{50}$ is 10 nm or less.

Namely, when the photon energy is E and the bandgap energy is Eg, the absorption constant $\alpha$ is represented by equation (2).

$$\alpha = A\frac{(E-Eg)^{1/2}}{E} \tag{2}$$

Here, A is a constant.

Equation (2) can be rewritten into equation (3).

$$(\alpha E)^2 = A(E-Eg) \tag{3}$$

FIG. 5 is an $E$-$(\alpha E)^2$ characteristic diagram to be obtained from an absorption spectrum, wherein the abscissa indicates the photon energy E and the ordinate indicates the $(\alpha E)^2$.

As shown in FIG. 5, when a tangent A is drawn to the ascent curve part of the $E$-$(\alpha E)^2$ characteristic diagram, the point $((\alpha E)^2 = 0)$ at which the tangent A intersects the X-axis indicates a bandgap energy Eg1 of the ultrafine ZnO particles.

It is generally known that when the particle diameter of a substance is brought closer to a nanometer level (10 nm or less), the bandgap energy will be increased by a quantum size effect.

Therefore, when the bandgap energy Eg1 is larger than the bandgap energy Eg of bulk ZnO, it means that the quantum size effect was developed and it is possible to confirm that the ultrafine ZnO particles 2 are micronized. Namely, when an absorption spectrum is measured, whether the average particle diameter $D_{50}$ of ultrafine ZnO particles is at a desired nanometer level (10 nm or less, preferably 5 nm or less) or not can be examined on the basis of an $E$-$(\alpha E)^2$ characteristic diagram obtained from the absorption spectrum measured.

When comparing primary surfactants 6 differing in the side chain length n of a hydrophilic group 6b by their transmission spectra and/or absorption spectra, the photon energy with which the decrease in optical transmittance I or the increase in absorption constant α starts will shift to the higher energy side if the side chain length n becomes larger and will shift to the lower energy side if the side chain length n becomes smaller. This is because if the particle diameter of ultrafine ZnO particles 2 is micronized, the bandgap energy will become larger. Therefore, the fact that the particle diameter varies depending upon the size of the side chain length n can be confirmed by measuring the transmission spectrum and/or an absorption spectrum without doing observation by TEM.

The ZnO dispersion 1 is formed by a hydrolysis reaction of a Zn alkoxide in a W/O type microemulsion solution.

In the following, a method for producing the dispersion solution is described.

When a hydrophobic solvent 1, a surfactant 3 (primary surfactant 6 and secondary surfactant 7) and water are charged into a container 5 and are mixed and stirred, the hydrophobic groups 6a of the primary surfactant 6 are adsorbed by the hydrophobic solvent 4, the hydrophilic groups 6b of the primary surfactant 6 are adsorbed by the water, and the secondary surfactant 6 enters into the hydrophilic groups 6b of the primary surfactant 6, as shown in FIG. 6(a), so that the interfacial energy with the water decreases. As a result, the water becomes water drops 8 having an ultrafine diameter and is confined within the surfactant 3 (primary surfactant 6 and secondary surfactant 7). Namely, the water drops 8 are dispersed in the hydrophobic solvent 4 while being surrounded by the surfactant 3, and thereby a water-in-oil type microemulsion is formed.

The surfactant 3 and the water are charged into the container 5 while being blended so that the average particle diameter $D_{50}$ of ultrafine ZnO particles as a final product is 10 nm or less (preferably 5 nm or less), for example, a ratio water/surfactant is 0.005 to 0.05.

Next, a Zn alkoxide solution serving as a raw material of ultrafine ZnO particles is prepared.

In order to obtain ZnO particles 2 which are ultrafine and have a desired particle diameter such that the width of their particle size distribution is narrow, it is necessary to avoid causing an increase in the diameter of water drops 8 as a result of the hydrolysis reaction, and for this purpose it is preferable to use a nonahydrate such as a Zn alkoxide.

However, it is known that a Zn alkoxide will hardly dissolve in alcohol.

Thus, in the present embodiment, an aminoalcohol, preferably a primary $C_{1-10}$ alkanolamine, such as monoethanolamine ($H_2NCH_2CH_2OH$) which can make the Zn alkoxide dissolve in an alcohol and does not dissolve in the hydrophobic solvent 4 is used together with the Zn alkoxide. Namely, an aminoalcohol is dissolved in an alcohol such as ethanol and at the same time, a Zn alkoxide is added to the alcohol to dissolve, and thereby a Zn alkoxide solution is prepared.

It is preferable that the preparation of the Zn alkoxide solution be carried out in an inert atmosphere such as an Ar atmosphere from the viewpoint of preventing the moisture in the air from infiltrating into the Zn alkoxide solution. If the preparation of the Zn alkoxide solution is carried out in an inert atmosphere, excess moisture is prevented from infiltrating into the microemulsion and, as a result, it is possible to inhibit the particle diameter of ultrafine ZnO particles from becoming large.

It is necessary that the molar amount of the aminoalcohol added to the alcoholic medium is at least the same as the molar amount of the zinc alkoxide added to the alcoholic medium. This is because if the molar amount of an aminoalcohol added to an alcohol is less than the molar amount of the added Zn alkoxide, the Zn alkoxide, which is a solid, does not dissolve thoroughly in the alcoholic medium and some undissolved Zn alkoxide remains.

Next, the thus-prepared Zn alkoxide solution is added to the microemulsion and is stirred and mixed under an inert atmosphere such as an Ar atmosphere for a prescribed time period. A hydrolysis reaction occurs between the Zn alkoxide and water of drops 8.

For example, when diethoxy Zn is used as the Zn alkoxide, a hydrolysis reaction like that shown in a chemical reaction formula (B) occurs and ultrafine ZnO particles 2 having an ultrafine diameter are formed.

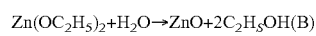

$$Zn(OC_2H_5)_2 + H_2O \rightarrow ZnO + 2C_2H_5OH \quad (B)$$

The hydrolysis reaction advances by using a water drop 8 surrounded by a surfactant 3 as a reaction field, so that the water drop 8 is consumed and eventually a transparent ultrafine ZnO particle 2 is formed as illustrated in FIG. 6(b).

The Zn alkoxide solution is dropped into the microemulsion solution so that the amount of water in the microemulsion solution is 1 to 1.2 times the amount of water required for the hydrolysis of the Zn alkoxide. This is because if the amount of water in the microemulsion is less than one time the amount of water needed for the hydrolysis of the Zn alkoxide, the desired hydrolysis reaction does not advance, whereas if it exceeds 1.2 times, the amount of water becomes large, so that the water drop 8 becomes large and, as a result, the average particle diameter $D_{50}$ of resulting ZnO may become larger to conform to the increased water drop diameter.

The kind of the Zn alkoxide is not restricted to the diethoxy Zn and, needless to say, dipropoxy Zn, dibutoxy Zn and the like, can be used.

In the present embodiment, by the use of a Zn alkoxide prepared by using aminoalcohol, the Zn alkoxide is hydrolyzed by using as a reaction field a water drop 8 having an ultrafine diameter which is not in contact with other water drops 8 and which is in a monodispersed state. Therefore, ultrafine ZnO particles 2 having an ultrafine diameter restricted by the water drop diameter exists while being dispersed and floating stably with the particles surrounded by a surfactant. Thereby, it is possible to obtain a ZnO dispersion 1 in which single-crystal ultrafine ZnO particles 2 having an average particle diameter $D_{50}$ of 10 nm or less (preferably 5 nm or less), an extremely narrow particle size distribution with a ratio $\sigma/D_{50}$ of 0.2 or less, and a high crystallinity are dispersed without causing agglomeration/sedimentation of particles.

Moreover, the present embodiment does not need a high-temperature and high-pressure environment as in a hydrothermal synthesis process and also does not need be carried out hydrolysis slowly over several days as in a sol-gel process. Therefore, it is possible to obtain a dispersion solution 1 in which desired ultrafine ZnO particles are dispersed in a relatively short time without requiring large-scale equipment.

Since the reaction is carried out by using water in a necessary minimum amount, it is possible to inhibit the incorporation of a hydroxyl group into the ultrafine ZnO particle 2 or the development of a defect. Moreover, it is possible to control the particle diameter of ultrafine ZnO particles to be formed by changing the side chain length n of a hydrophilic group 6b of a primary surfactant 6 to be used, and therefore it is possible to simply prepare a ZnO dispersion with a high quality according to an intended application.

Next, a ZnO thin film prepared by using this dispersion solution 1 is explained in detail.

Figure 7:
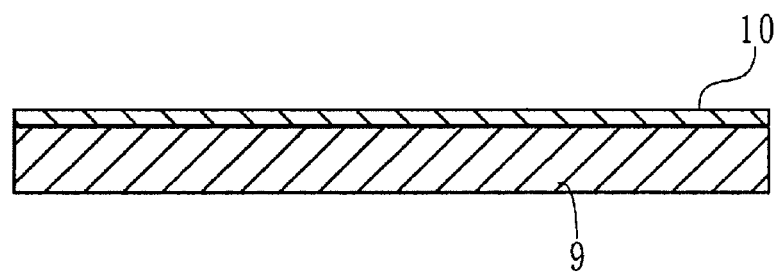
FIG. 7 is a sectional view schematically showing one embodiment of the ZnO thin film according to the present invention.

FIG. 7 is a sectional view schematically showing one embodiment of the ZnO thin film, and a ZnO thin film 10 formed by using the ZnO dispersion 1 has been formed on a substrate 9 such as a quartz substrate.

Figure 8:
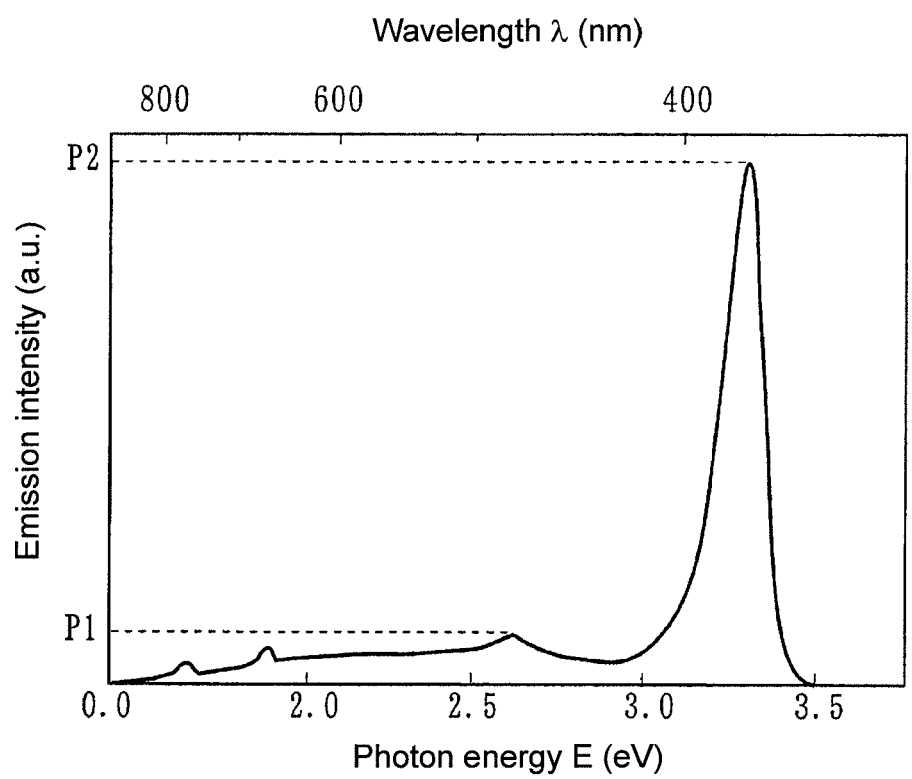
FIG. 8 is a diagram showing one example of the fluorescence spectrum of the ZnO thin film of the present invention.

As a result of being produced by using the ZnO dispersion 1, the ZnO thin film 10 satisfies a ratio of a maximum emission intensity P1 in a visible range (2.0 to 2.8 eV) to a maximum emission intensity P2 in an ultraviolet range (2.8 eV or more), P1/P2, of 0.2 or less in the fluorescence spectrum shown in FIG. 8.

The ordinate in FIG. 8 indicates the emission intensity P (a.u.), the lower abscissa indicates the photon energy E (eV) and the upper abscissa indicates the wavelength $\lambda$ (nm).

Thus, since the ZnO thin film 10 is characterized in that the ratio of a maximum emission intensity P1 in a visible range to a maximum emission intensity P2 in an ultraviolet range, P1/P2, is 0.2 or less, visible emission caused by the level of defects, such as oxygen defect, is emitted weakly and ultraviolet emission caused by interband transition or exciton recombination is emitted strongly, and thereby a ZnO thin film 10 having few defects and a high crystallinity can be obtained.

The ZnO thin film 10 can be produced easily by applying the ZnO dispersion 1 uniformly to the substrate 9 by a spin coating process or the like and then performing a heat treatment.

Namely, the dispersion solution 1 is applied, for instance, to the substrate 9 uniformly by dropping the dispersion solution 1 on the substrate 9 and then rotating the substrate 9 at a prescribed speed for a prescribed time period. After that, by performing a heat treatment at a temperature of, for example, 250 to 700° C., the hydrophobic solvent 4, the primary surfactant 6, and so on, are evaporated away, whereas ultrafine ZnO particles are grown by heat, and thereby it is possible to produce a desired ZnO thin film 10 easily.

Since a ZnO dispersion 1 in which ultrafine ZnO particles in a single crystal state are dispersed is used in this embodiment, a ZnO thin film 10 which maintains a single crystal and is excellent in crystallinity can be obtained. Moreover, since a thin film is formed by growing single crystal particles by a heat treatment, no cracks are formed in the film, unlike a sol-gel process. Namely, it is possible to obtain a high quality ZnO thin film 10 which is free from defects, capable of exhibiting strong ultraviolet emission, high in crystallinity, and high in visible light transmittance.

Moreover, since single crystal particles in the ZnO thin film 10 have been grown by a heat treatment, the particle diameter can be controlled by only changing the heat treatment temperature and an ultrafine ZnO particle thin film useful for the production of an ultraviolet emission device and a quantum device can be obtained simply by low-temperature film formation.

It is needless to say that the present invention is not limited to the embodiments described above and can be modified without departure from the gist thereof.

Moreover, as an application example of the present invention, it is possible to realize a ZnO dispersion of core-shell structure in which ZnO is surrounded by a shell of an inorganic compound or an organic polymer and a surfactant, by stirring a composite alkoxide solution of Zn and a metal alkoxide other than Zn (e.g., Al, Sn, Si, Ti, Cd, Se, S and Cu) and/or an organic polymer solution in a microemulsion. The present invention can also be extended to a ZnO dispersion of such core-shell structure. By the realization of a ZnO dispersion of such core shell structure, it becomes possible to obtain ultrafine ZnO particles having properties which mere ultrafine ZnO particles cannot develop, and it becomes possible to provide a dispersion solution excellent in dispersibility, durability and storability.

Next, Examples of the present invention are described in detail below.

Example 1

Dispersion were produced by using primary surfactants differing in the side chain hydrophilic group length n and material characteristics were evaluated.

Production of Samples

Cyclohexane was used as a hydrophobic solvent, 1-octanol was used as a secondary surfactant, and water was further used.

Four NPE(n)s having side chain hydrophilic group lengths n of 2, 4, 10 and 15, respectively, were prepared as primary surfactants.

Then, the cyclohexane, NPE(n), 1-octanol and water were mixed and stirred so as to achieve a ratio of 30:1.4:1.7:0.03, thereby producing a W/O type microemulsion.

Next, diethoxy Zn was used as a Zn alkoxide, monoethanolamine was used as an aminoalcohol, ethanol was used, and these were mixed and stirred to prepare a diethoxy Zn solution (Zn alkoxide solution) was prepared.

Specifically, the same molar amount of monoethanolamine as the molar amount of the diethoxy Zn added to the ethanolic solution was added first to the ethanolic solution to produce a mixed solvent. Subsequently, in a glove box under an Ar atmosphere, diethoxy Zn was added to the mixed solvent and then mixed and stirred to produce a diethoxy Zn solution.

When the added amount of monoethanolamine was reduced to an amount less than the added molar amount of diethoxy Zn, the diethoxy Zn failed to thoroughly dissolve in the mixed solvent. Namely, it was confirmed that monoethanolamine in a molar amount at least equal to that of diethoxy Zn was needed in order to dissolve diethoxy Zn thoroughly in the mixed solvent.

Next, the diethoxy Zn solution was dropped into four microemulsions with a micropipet so that the amount of water in the microemulsion solution was 1.2 times the amount of water necessary for the hydrolysis of the diethoxy Zn. By stirring and mixing overnight in a glove box containing an Ar atmosphere, dispersion of Sample Nos. 1 to 4 were produced.

The resulting dispersion were perfectly transparent, and even though they were stored for several weeks while being hermetically sealed, their transparent state was not damaged.

As to the primary surfactants, Sample No. 1, Sample No. 2, Sample No. 3 and Sample No. 4 correspond to NPE(2), NPE(4), NPE(10) and NPE(15), respectively.

Measurement of Transmission Spectrum and Absorption Spectrum

The transmission spectra of Sample Nos. 1 to 4 were measured by using an absorptiometer (UV-2500PC, manufactured by Shimadzu Corporation).

Figure 9:
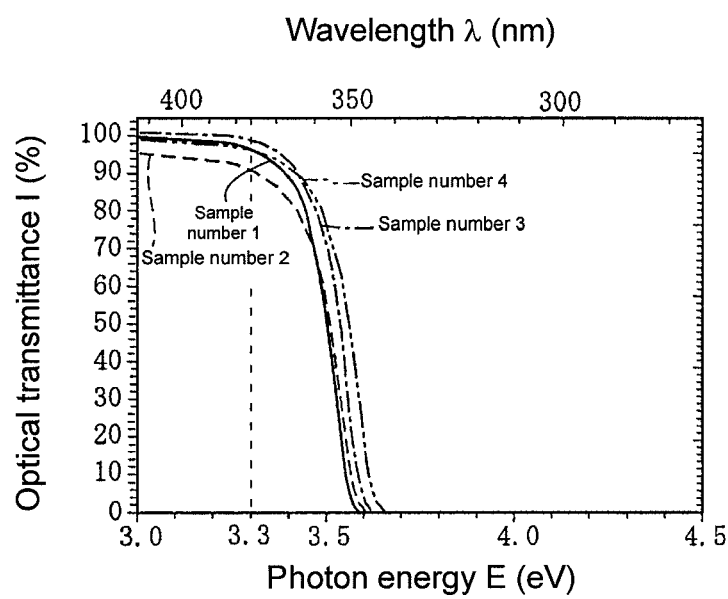
FIG. 9 is a diagram showing the transmission spectra of individual samples in Example 1.

The measurement results are shown in FIG. 9. The ordinate indicates the optical transmittance (%), the lower abscissa indicates the photon energy E (eV), and the upper abscissa indicates the wavelength λ (nm). In the diagram, the solid line indicates Sample No. 1, the broken line indicates Sample No. 2, the long dashed short dashed line indicates Sample No. 3 and the long dashed double-short dashed line indicates Sample No. 4.

As is clear from FIG. 9, the optical transmittance I decreases rapidly approximately from the point where the photon energy E exceeds 3.3 eV although an extremely high optical transmittance I of 90 to 100% is maintained up to 3.3 eV which is the bandgap energy Eg of the bulk ZnO.

This showed that ZnO existed in the dispersion solution.

Next, samples of Sample Nos. 1 to 4 were diluted 10 fold with low-moisture cyclohexane solutions, and the absorption spectra of the diluted samples were measured by using the absorptiometer.

Figure 10:
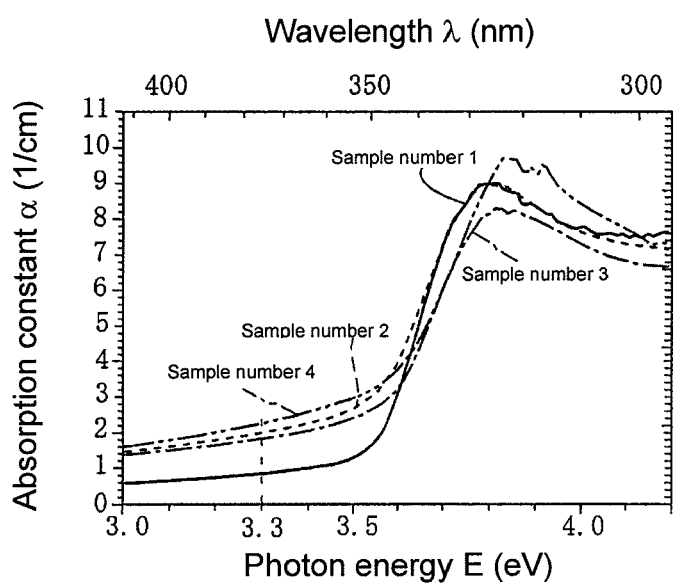
FIG. 10 is a diagram showing the absorption spectra of individual samples in Example 1.

The measurement results are shown in FIG. 10. The ordinate indicates the absorption constant α (1/cm), the lower abscissa indicates the photon energy E (eV) and the upper abscissa indicates the wavelength λ (nm). In the diagram, the solid line indicates Sample No. 1, the broken line indicates Sample No. 2, the long dashed short dashed line indicates Sample No. 3 and the long dashed double-short dashed line indicates Sample No. 4.

As is clear from FIG. 10, the absorption constant α increases rapidly since the photon energy E exceeds the bandgap energy Eg (=3.3 eV) of the bulk ZnO. When the bandgap energies Eg1 of Sample Nos. 1 to 4 were determined by the method shown in FIG. 5, it was confirmed that they exceeded 3.5 eV. Namely, it was confirmed that a quantum size effect was developed and it became clear that the ultrafine ZnO particles had ultrafine diameters of nanometer level.

Using primary surfactants whose side chain lengths n were longer in order of Sample Nos. 1 to 4 were used, it was found that the photon energy E with which the decrease in optical transmittance I or the increase in absorption constant α started shifted to the high energy side with an increase in side chain length n and shifted to the low energy side with a decrease in side chain length n. Namely, the transmission spectrum and/or the absorption spectrum revealed that the particle diameter varied depending upon the length of the side chain length n.

Particle Diameter of Sample, Identification of Sample, and Particle Size Distribution Each sample of Sample Nos. 1 to 4 was dropped and dried on a Cu mesh with carbon film for TEM, and was observed by TEM.

Figure 11:
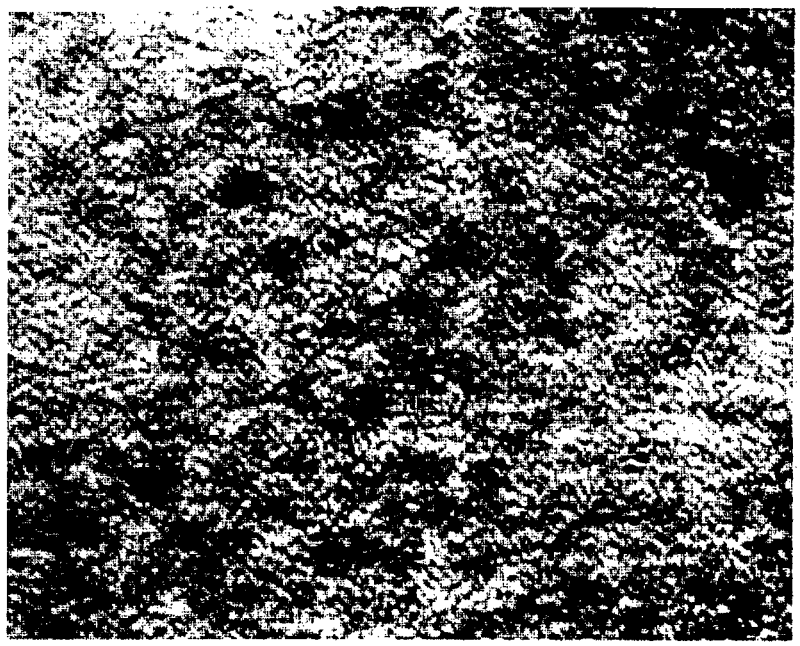
FIG. 11 is a TEM image of Sample No. 1.
Figure 12:
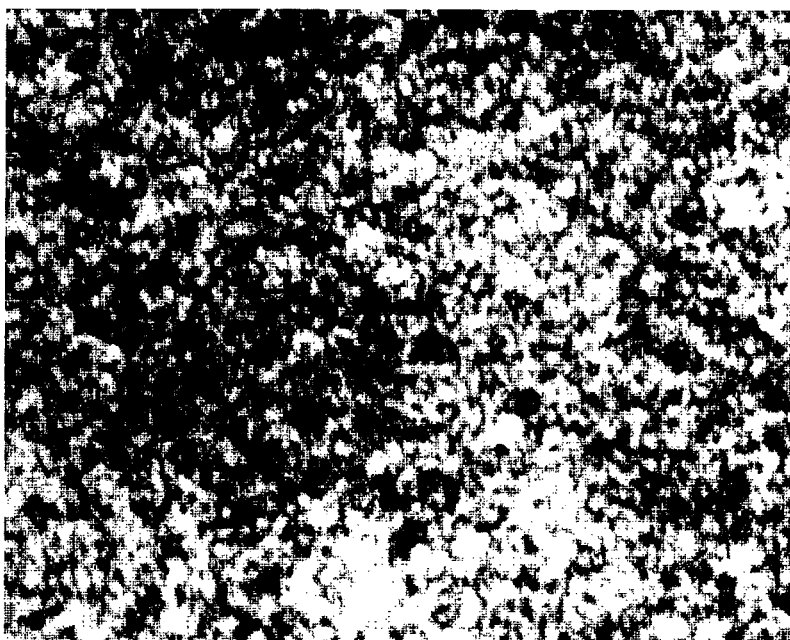
FIG. 12 is a TEM image of Sample No. 2.
Figure 13:
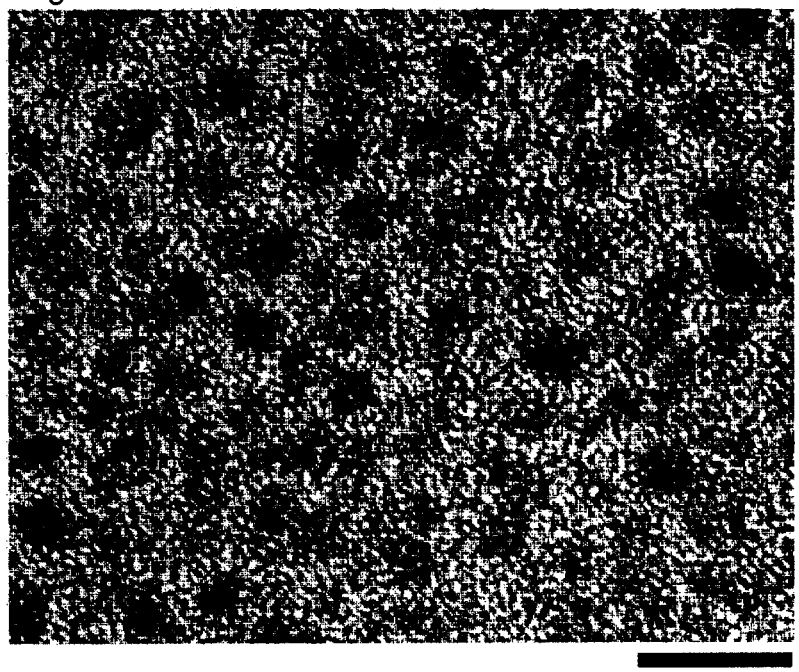
FIG. 13 is a TEM image of Sample No. 3.
Figure 14:
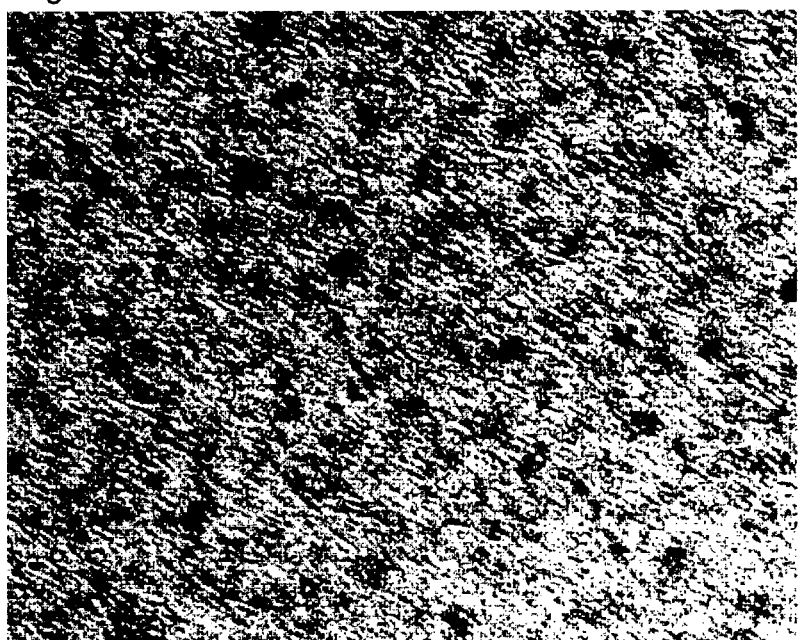
FIG. 14 is a TEM image of Sample No. 4.
Figure 15:
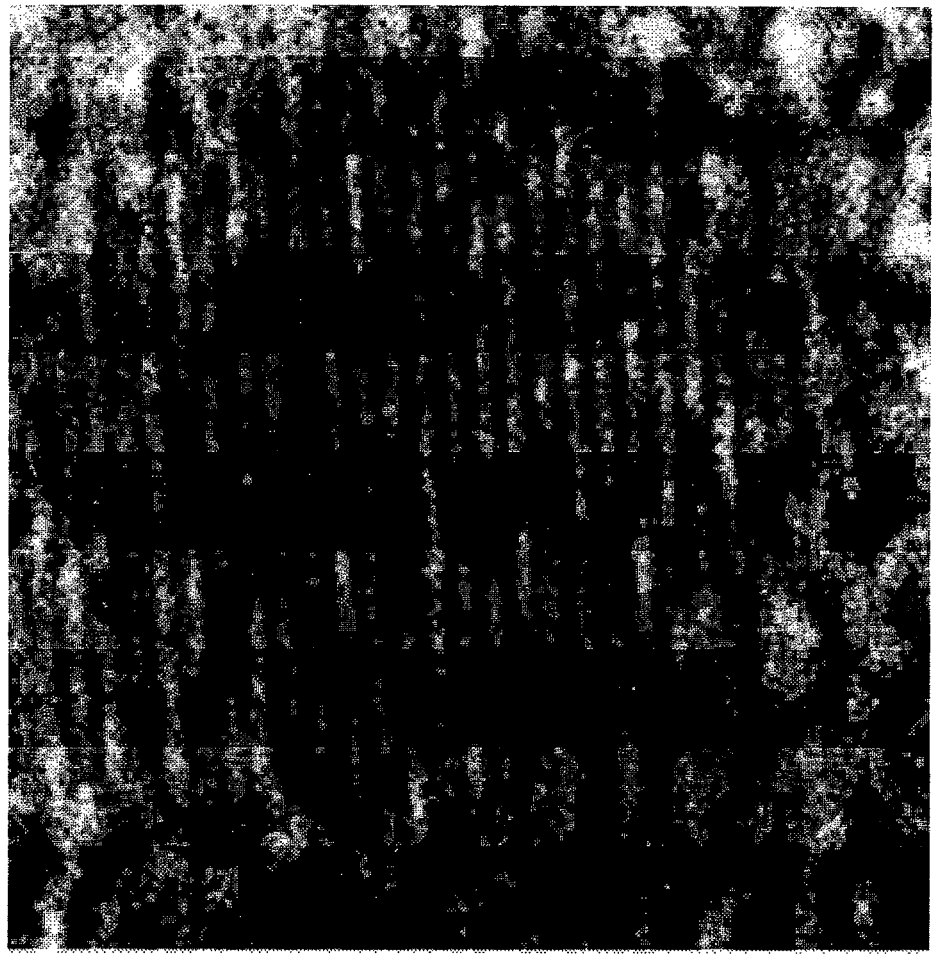
FIG. 15 is an enlarged TEM image of Sample No. 3.

FIG. 11 shows the TEM image of Sample No. 1, FIG. 12 shows the TEM image of Sample No. 2, FIG. 13 shows the TEM image of Sample No. 3 and FIG. 14 shows the TEM image of Sample No. 4. FIG. 15 is an enlarged TEM image of Sample No. 3 (FIG. 13).

From FIG. 11 to FIG. 15, it could recognize visually that they were all ultrafine particles as small as 5 nm or less and single-crystallized ZnO was formed without agglomerating. Moreover, it was found that the particle diameter became smaller with increase in side chain length n of the hydrophilic group and therefore, the particle diameter could be controlled by the side chain length n of the hydrophilic group.

Next, selected area electron diffraction images were taken by using TEM.

Figure 16:
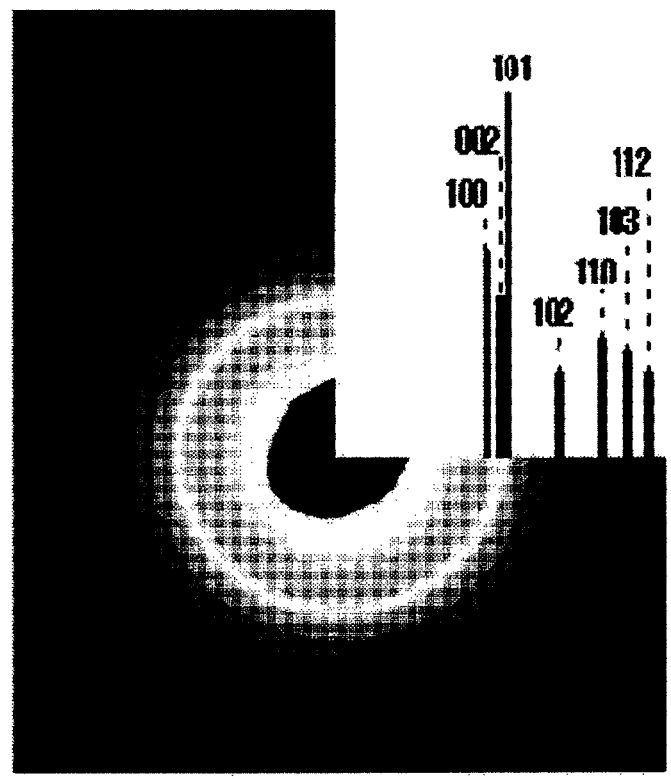
FIG. 16 is a selected area electron diffraction image of Sample No. 3.
Figure 17A:
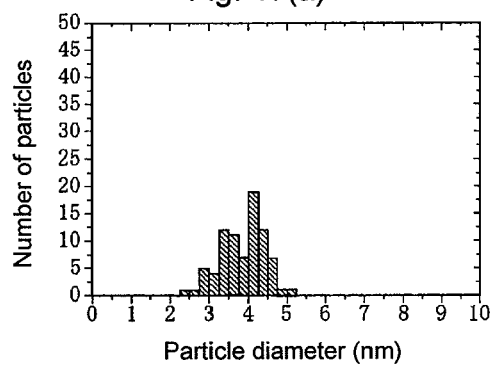
FIGS. 17(a) to 17(d) show the particle size distributions of the ultrafine ZnO particles of individual samples in Example 1.
Figure 17C:
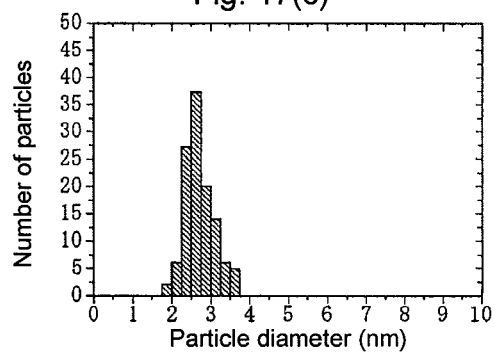
Figure 17B:
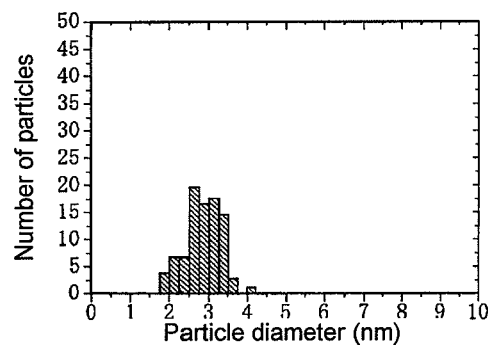
Figure 17D:
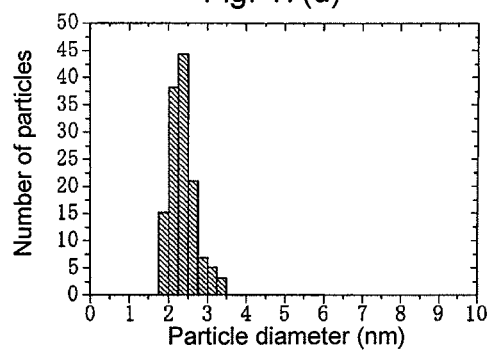

FIG. 16 shows the selected area electron diffraction image of Sample No. 3, and the inserted diagram drawn in the right upper of FIG. 16 shows the electron diffraction pattern of wurtzite structure ZnO. The ordinate of the inserted diagram indicates the diffraction intensity (a.u.) of electron beams and the abscissa indicates the diffraction angle 2θ (deg). In the diagram, (100), (002) . . . indicate the indices of crystal plane of ZnO.

The position of the Debye ring shown in the selected area electron diffraction image agrees with the diffraction peak position of the wurtzite structure ZnO. Therefore, it was identified that the ultrafine particles in the sample were ZnO.

Next, the average particle diameter $D_{50}$, standard deviation σ and ratio $σ/D_{50}$ were determined from the individual TEM images of FIG. 11 to FIG. 14 by sampling many ultrafine ZnO particles.

Table 1 shows the type of the primary surfactants used in Sample Nos. 1 to 4, the total sample number N, the average particle diameter $D_{50}$ (nm), the standard deviation σ and the ratio $σ/D_{50}$.

TABLE 1

| Sample No. | Primary surfactant | Total number of samples N (samples) | Average particle diameter $D_{50}$ (nm) | Standard deviation σ (—) | $σ/D_{50}$ |
|---|---|---|---|---|---|
| 1 | NPE(2) | 81 | 3.85 | 0.56 | 0.15 |
| 2 | NPE(4) | 92 | 2.85 | 0.47 | 0.16 |
| 3 | NPE(10) | 117 | 2.69 | 0.38 | 0.14 |
| 4 | NPE(15) | 133 | 2.37 | 0.34 | 0.14 |

FIG. 17 shows particle size distributions of particle diameters of individual samples of Sample Nos. 1 to 4. FIG. 17(a) indicates particle size distribution of Sample No. 1, FIG. 17(b) indicates particle size distribution of Sample No. 2, FIG. 17(c) indicates particle size distribution of Sample No. 3, and FIG. 17(d) indicates particle size distribution of Sample No. 4.

As is clear from Table 1, ultrafine ZnO particles having an average particle diameter $D_{50}$ of 2.37 to 3.85 nm were obtained and the ratio $σ/D_{50}$ was 0.14 to 0.16, and it was found, as is clear from FIG. 17, that the particle size distributions were narrow. Namely, it was found that there were obtained ultrafine ZnO particles having an average particle diameter $D_{50}$ of 5 nm or less, having a narrow particle size distribution with a ratio $σ/D_{50}$ of 0.20 or less, being homogeneous, and existing in a single crystal state without agglomerating.

Comparative Example

A Comparative Example solution was produced by using no surfactant, and mixing and stirring cyclohexane and water so that their blended ratio was equal to the ratio in Example 1. After that, a diethoxy Zn solution was added to the Comparative Example solution by the same method and procedures as those described above. As a result, although ZnO particles were formed, the ZnO particles agglomerated and sedimented by being left at rest overnight.

As mentioned above, the predominance of the ZnO dispersion of this Example was confirmed.

Example 2

A ZnO thin film was produced by using the ZnO dispersion of Sample No. 3 of [Example 1], and material characteristics were evaluated.

Production of Samples

The dispersion solution was applied to a quartz substrate by a spin coating method, followed by heat treatment in the air at 250° C., 300° C., 350° C., 500° C. and 700° C. for a prescribed time period. Thus, samples of Sample Nos. 11 to 15 were produced.

Measurement of Transmission Spectrum

The transmission spectra of Sample Nos. 11 to 15 were measured by using the same absorptiometer as that used in Example 1.

Figure 18:
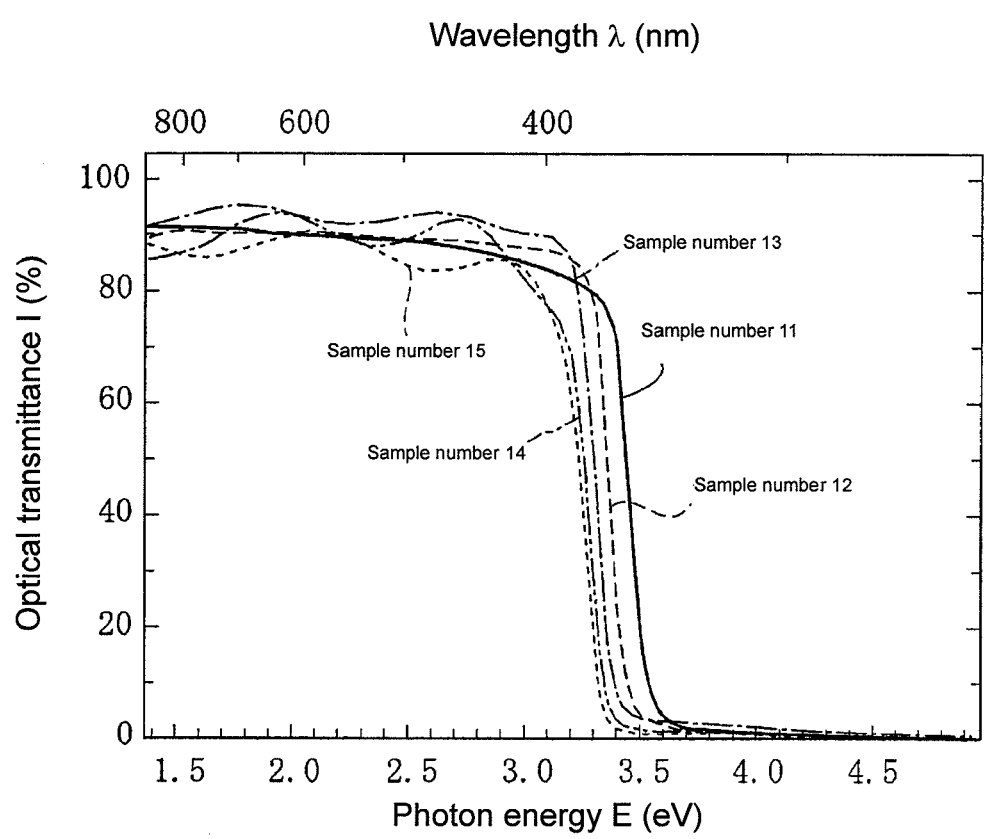
FIG. 18 is a diagram showing the transmission spectra of individual samples in Example 2.

The measurement results are shown in FIG. 18. The ordinate indicates the optical transmittance I (%), the lower abscissa indicates the photon energy E (eV), and the upper abscissa indicates the wavelength λ (nm). In the diagram, the solid line indicates Sample No. 11, the longer broken line indicates Sample No. 12, the long dashed short dashed line indicates Sample No. 13, the long dashed double-short dashed line indicates Sample No. 14, and the shorter broken line indicates Sample No. 15.

As is clear from FIG. 18, it was found that a high optical transmittance I of 80% or more was possessed in a visible region with a photon energy E of 3.0 eV or less without being depending on the heat treatment temperature.

X-ray Diffraction Spectra

The X-ray diffraction spectra of Sample Nos. 11 to 15 were measured by powder X-ray diffractometry by using an X-ray diffraction apparatus.

Figure 19:
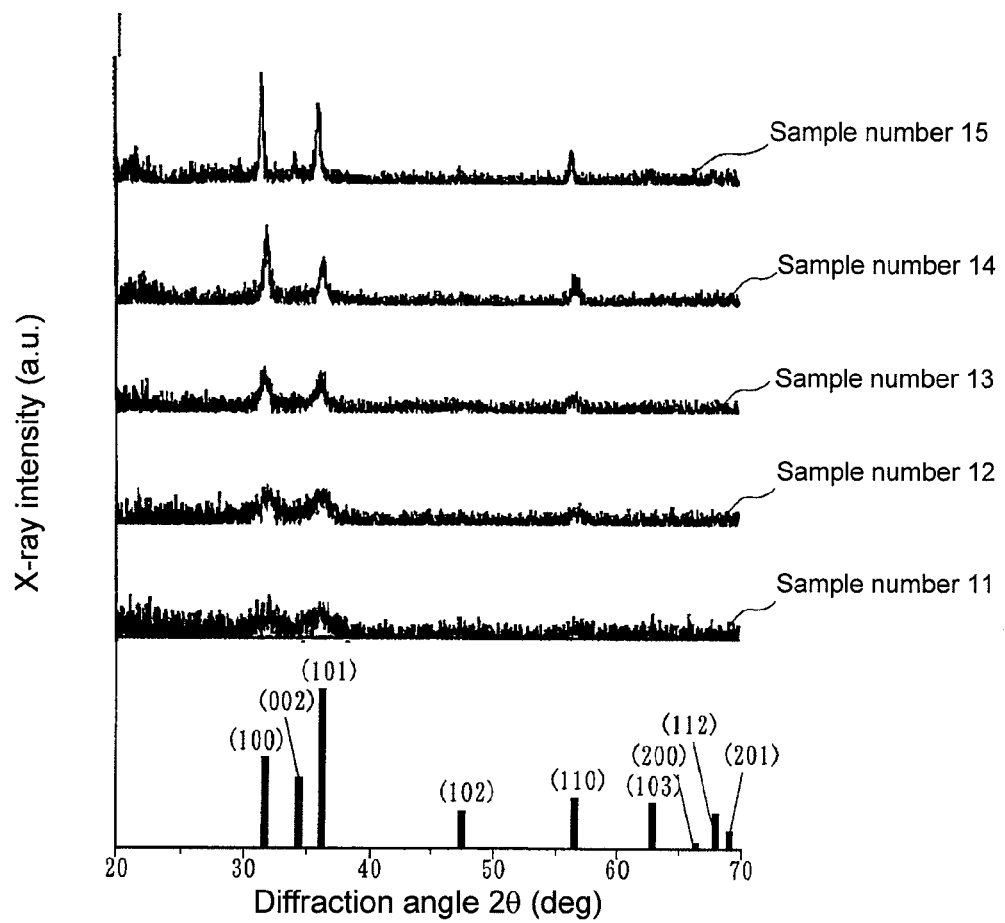
FIG. 19 is a diagram showing the X-ray diffraction patterns of individual samples in Example 2.

FIG. 19 shows the measurement results. The ordinate indicates the X-ray intensity (a.u.) and the abscissa indicates the diffraction angle 2θ (deg). In this diagram, the bar graph in the bottom part is an X-ray diffraction pattern of wurtzite structure ZnO.

As is clear from FIG. 19, each sample had a diffraction pattern like that of wurtzite structure ZnO and therefore it was found that crystallization advanced to a high degree without being influenced by the heat treatment temperature.

Measurement of Fluorescence Spectrum

Helium cadmium laser having a photon energy E of 3.8 eV (wavelength: 325 nm) was applied to the samples of Sample Nos. 11 to 15 and fluorescence spectrum was measured by using a spectrometer (TRIAX320 manufactured by SPEX).

Figure 20A:
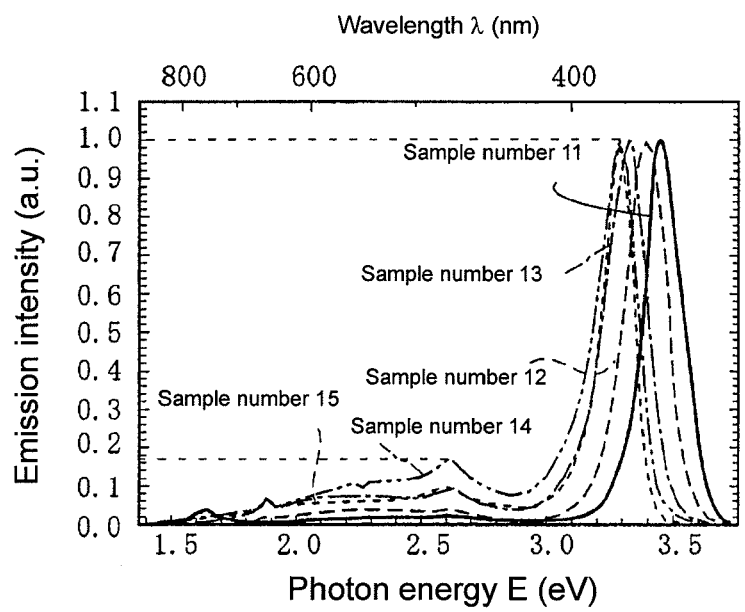
FIGS. 20(a) and 20(b) are diagrams showing the fluorescence spectra of individual samples in Example 2.
Figure 20B:
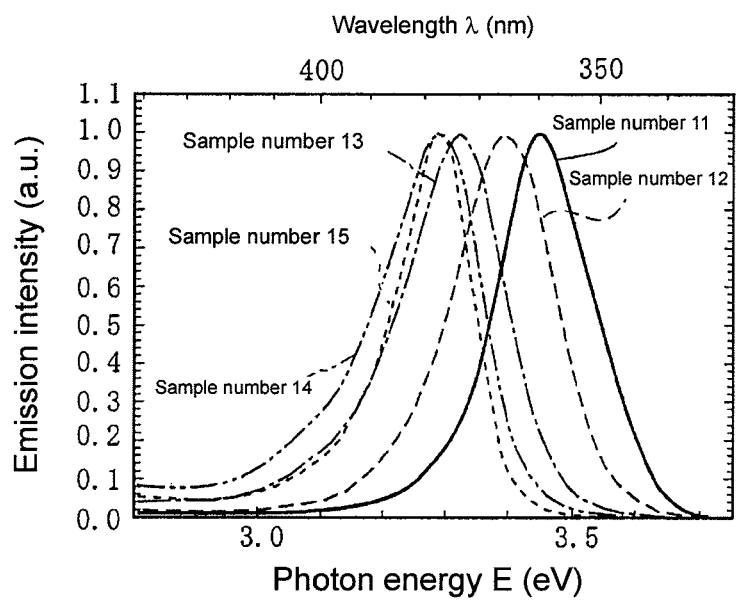

FIG. 20($a$) shows the fluorescence spectra, and FIG. 20($b$) was obtained by enlarging the ultraviolet region of FIG. 20($a$), wherein the maximum emission intensity was made 1.0 and the measured values were normalized between 0 and 1.0. The ordinate indicates the emission intensity P (a.u.), the lower abscissa indicates the photon energy E (eV) and the upper abscissa indicates the wavelength λ (nm). In the diagram, the solid line indicates Sample No. 11, the longer broken line indicates Sample No. 12, the long dashed short dashed line indicates Sample No. 13, the long dashed double-short dashed line indicates Sample No. 14 and the shorter broken line indicates Sample No. 15.

As is clear from FIG. 20, the maximum emission intensity P2 in a ultraviolet range where the photon energy E is 2.8 to 3.6 eV is 1.0, whereas the maximum emission intensity P1 in a visible range where the photon energy E is 2.0 to 2.8 eV is about 0.17, so that the ratio P1/P2 is 0.20 or less. Therefore, the P1/P2 ratio satisfies the present invention range of 0.20 or less.

Namely, it was confirmed that the samples exhibited strong ultraviolet emission due to interband transition or exciton recombination and that the visible emission derived from oxygen vacancy was weak, and this made it clear that a ZnO thin film being good in crystallinity and having few defects could be obtained.

In particular, it was found that Sample Nos. 11 and 12, which were produced at low heat treatment temperatures of 250° C. and 300° C., respectively, emitted weak visible emission and ultraviolet emission became dominant.

In the comparison of the wavelengths of the ultraviolet emissions emitted by the individual films, it is noted that the lower the heat treatment temperature of a thin film, the more the ultraviolet emission wavelength shifted to the shorter wavelength side. This means that the ultrafine ZnO particles forming a thin film have a sufficiently ultrafine diameter for developing a quantum size effect. Namely, it has been confirmed that the ZnO thin film heat-treated at a low temperature has a sufficiently ultrafine diameter for developing a quantum size effect.

Observation of Samples

For the individual samples of Samples 11 to 15, the surface image and the sectional image of a sample were observed by a scanning electron microscope (henceforth referred to as "SEM").

Figure 21:
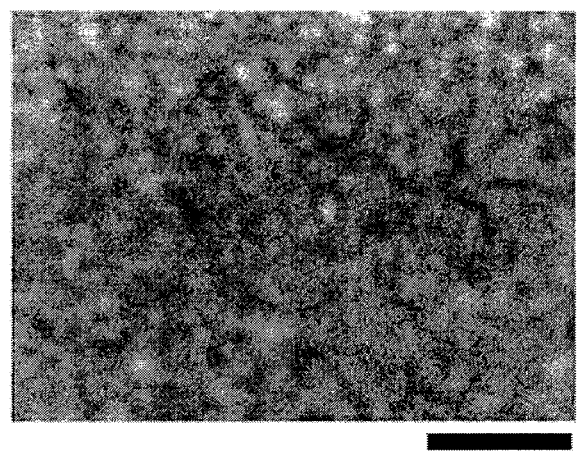
FIG. 21 is a SEM surface image of Sample No. 11.
Figure 22:
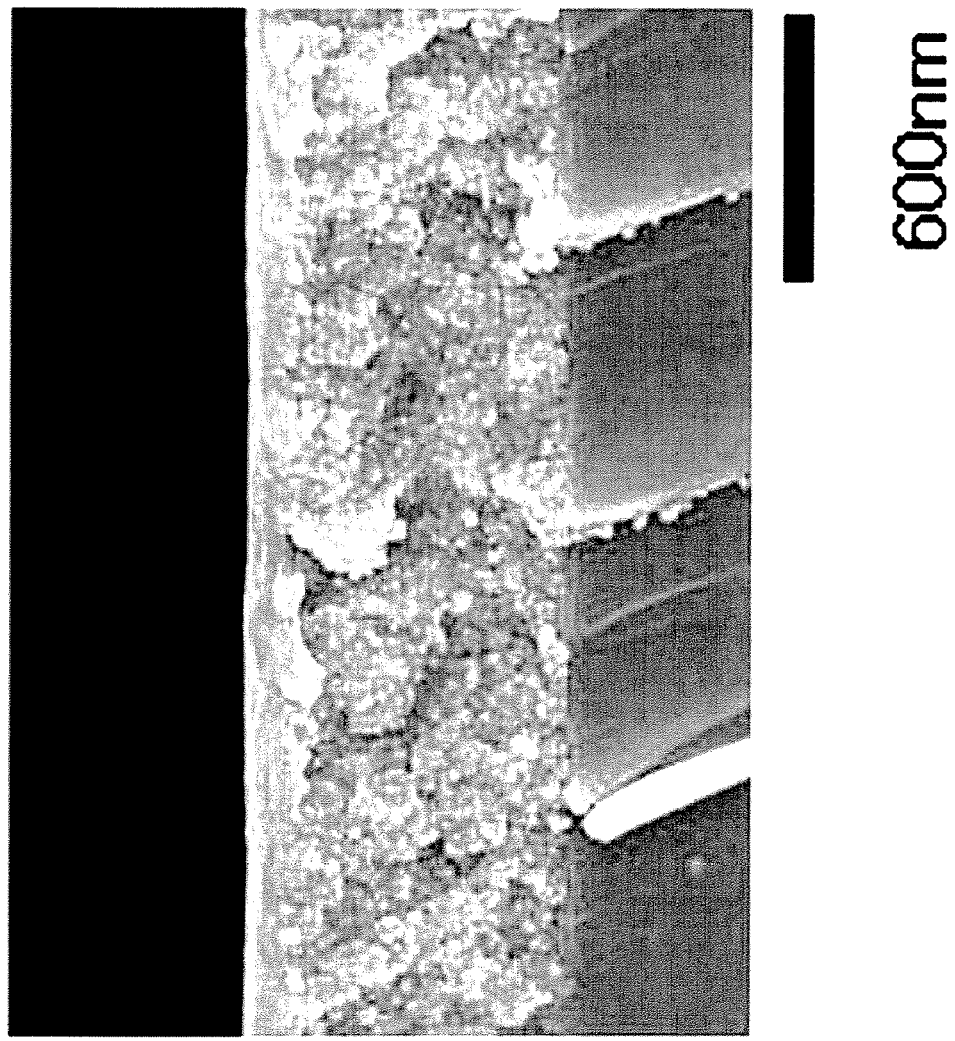
FIG. 22 is a SEM sectional image of Sample No. 11.
Figure 23:
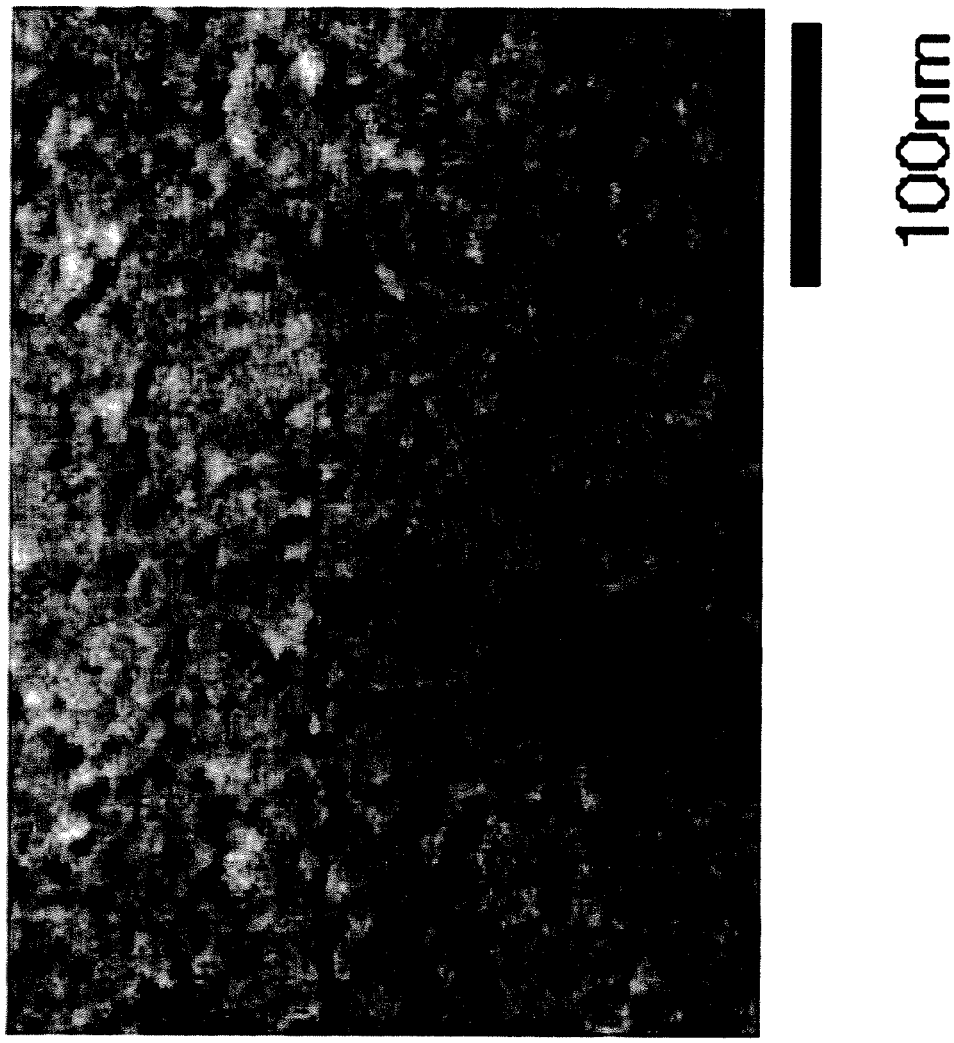
FIG. 23 is a SEM surface image of Sample No. 12.
Figure 24:
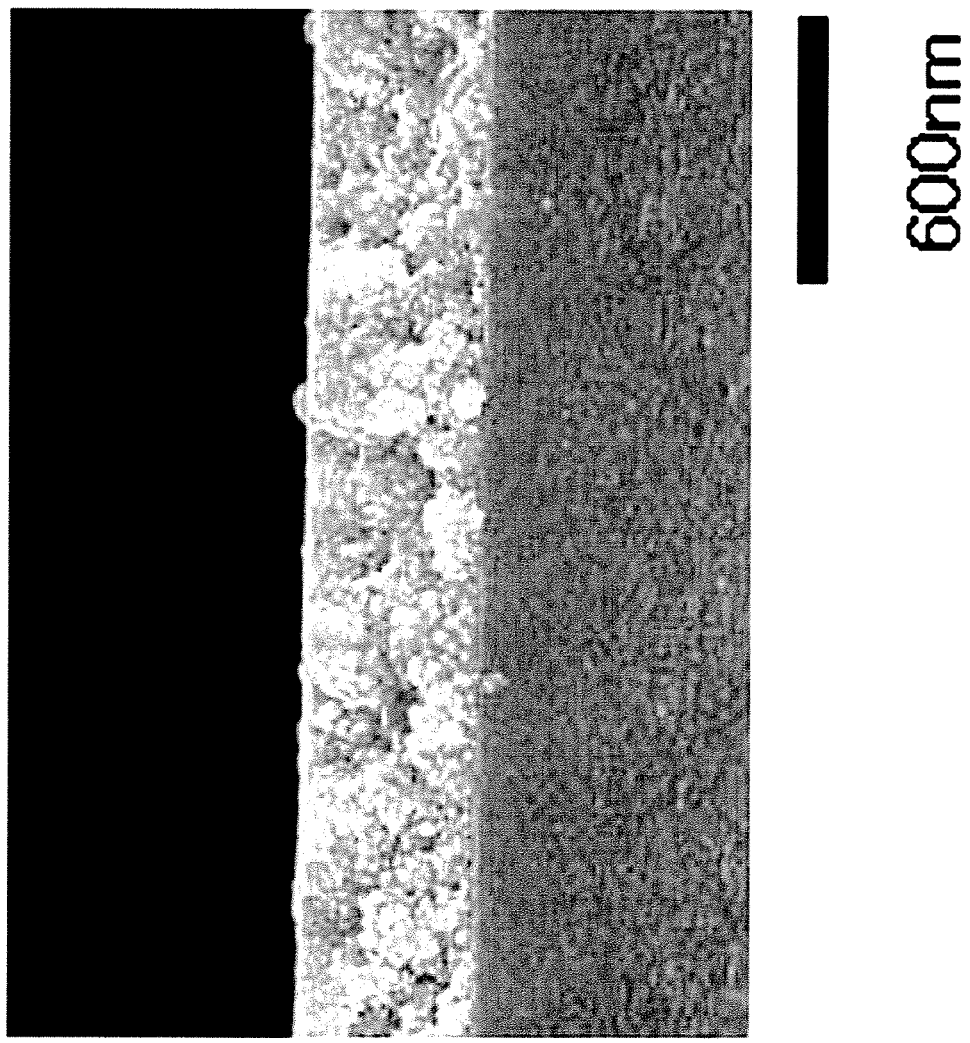
FIG. 24 is a SEM sectional image of Sample No. 12.
Figure 25:
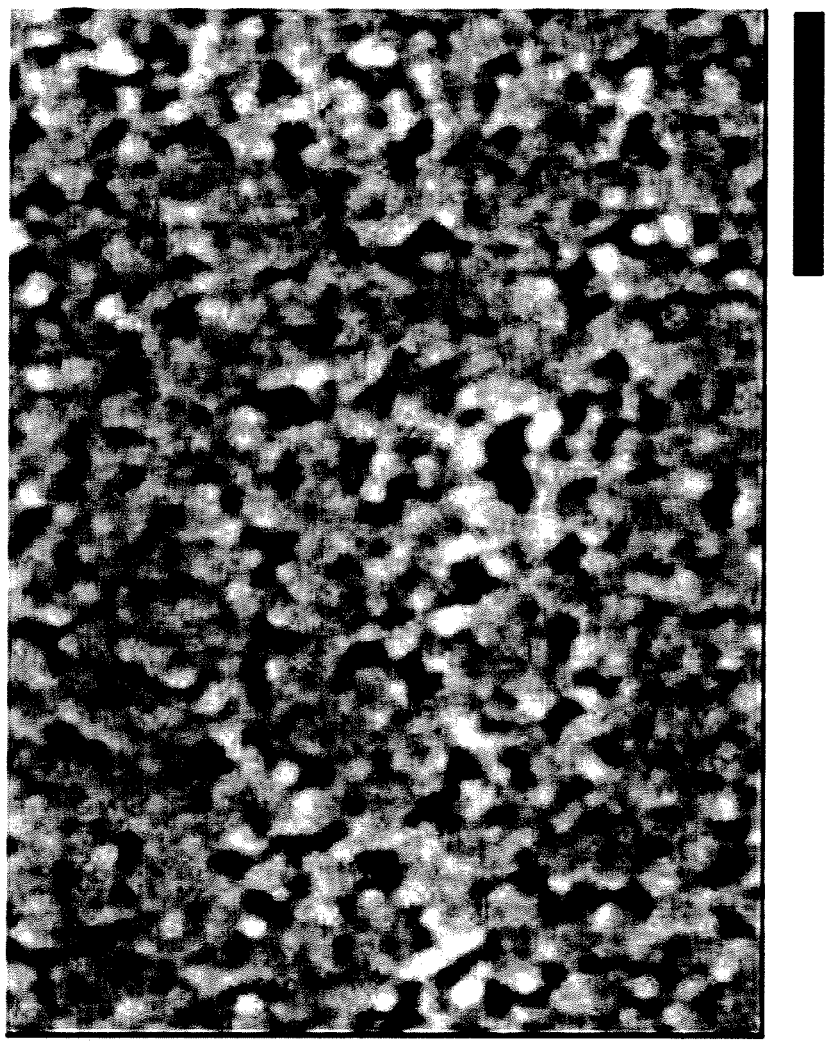
FIG. 25 is a SEM surface image of Sample No. 13.
Figure 26:
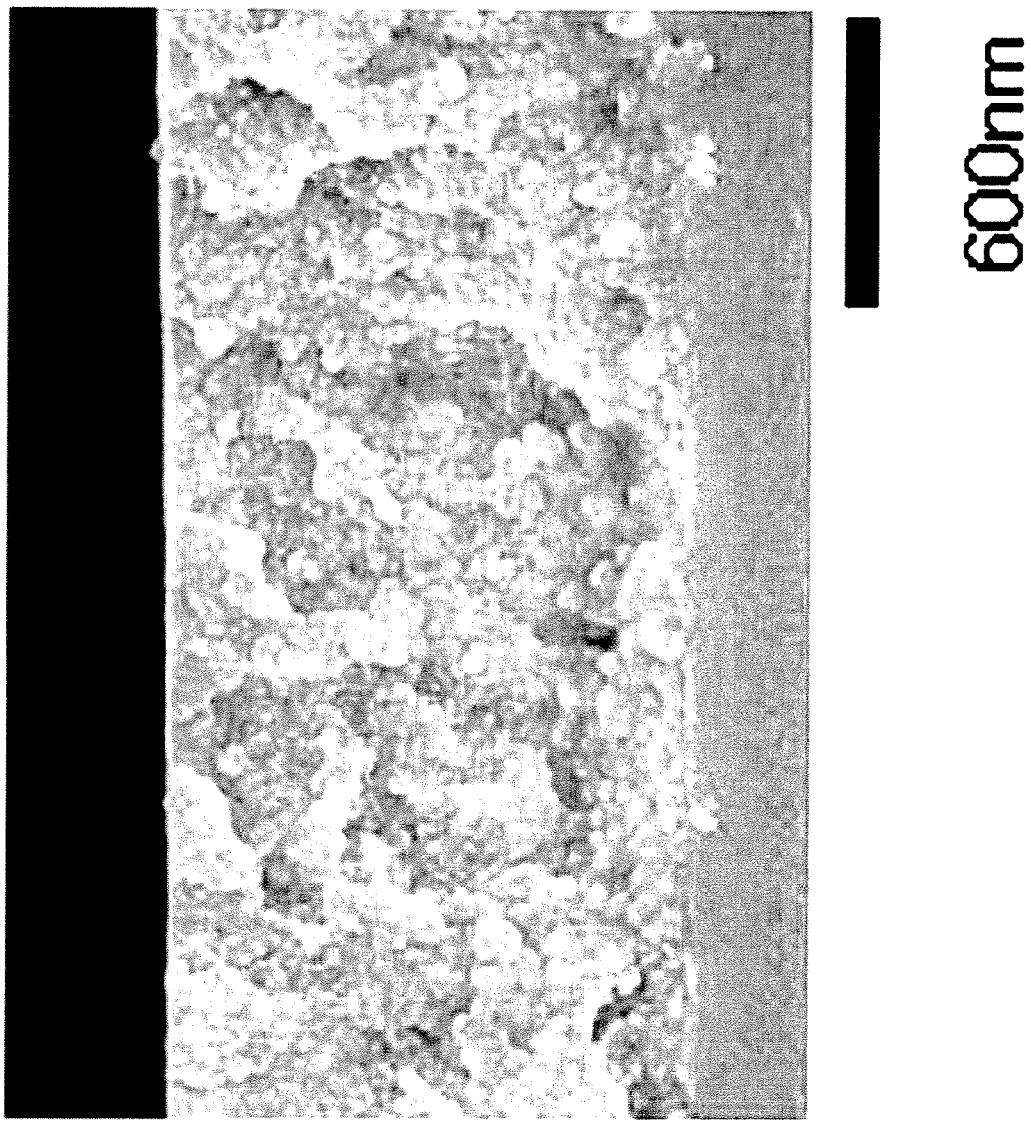
FIG. 26 is a SEM sectional image of Sample No. 13.
Figure 27:
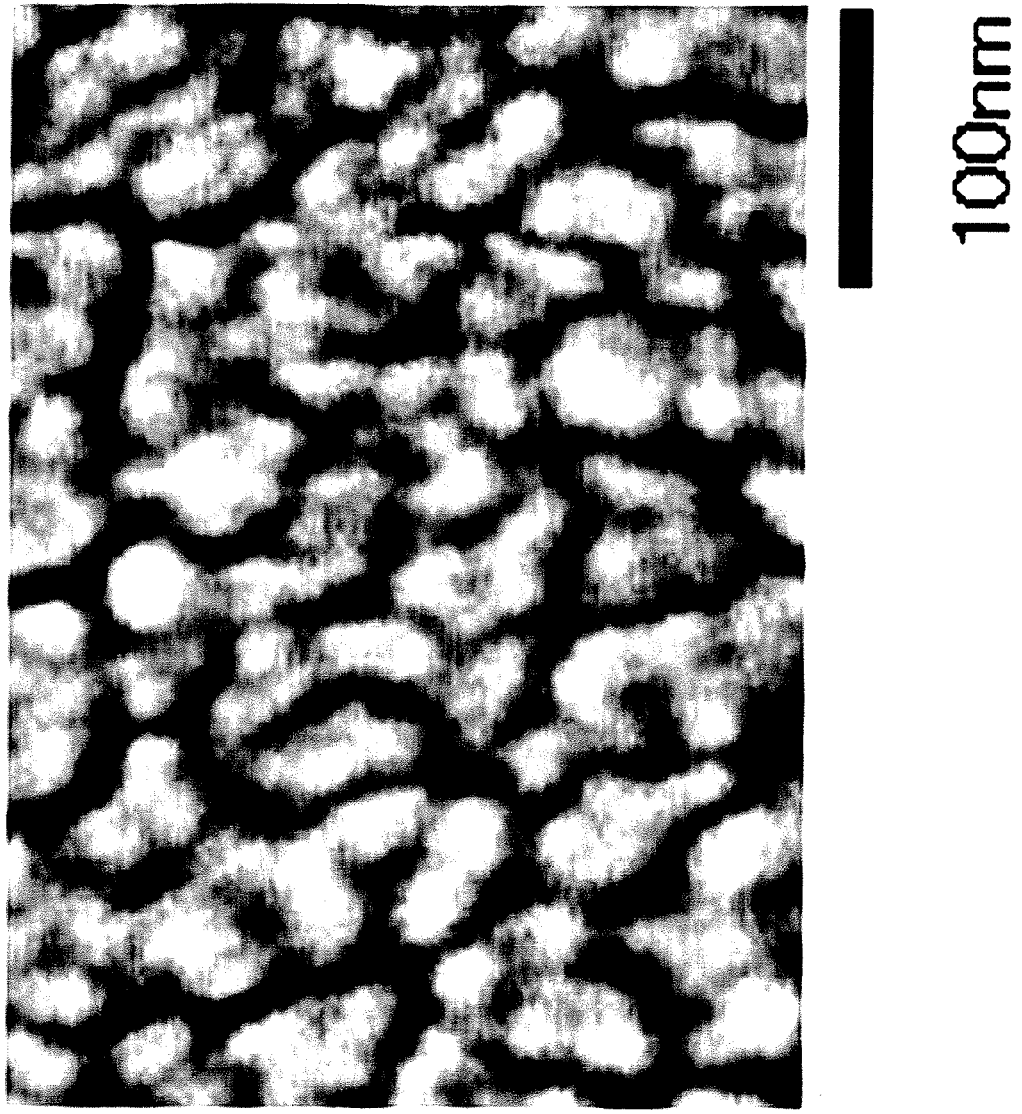
FIG. 27 is a SEM surface image of Sample No. 14.
Figure 28:
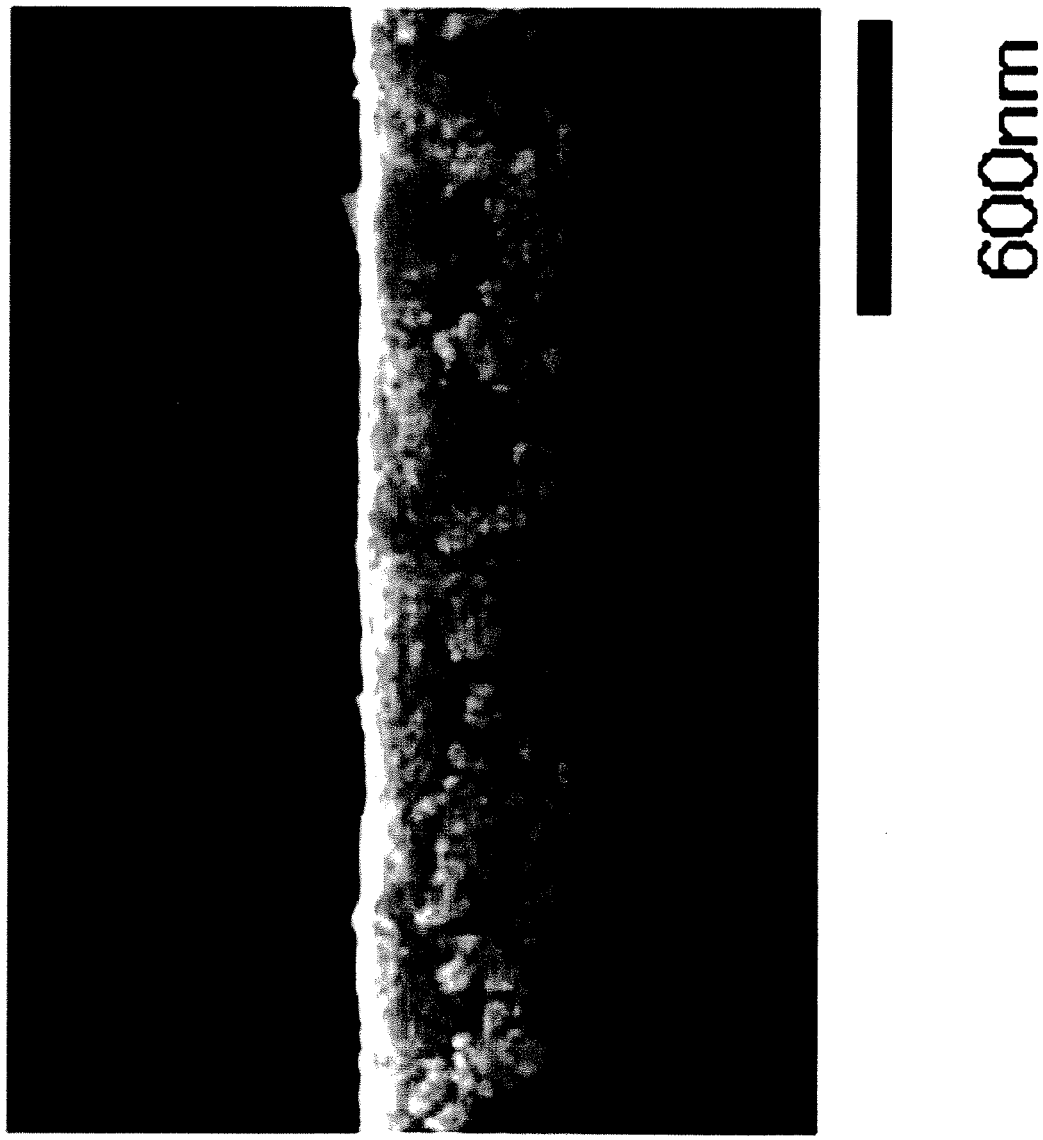
FIG. 28 is a SEM sectional image of Sample No. 14.
Figure 29:
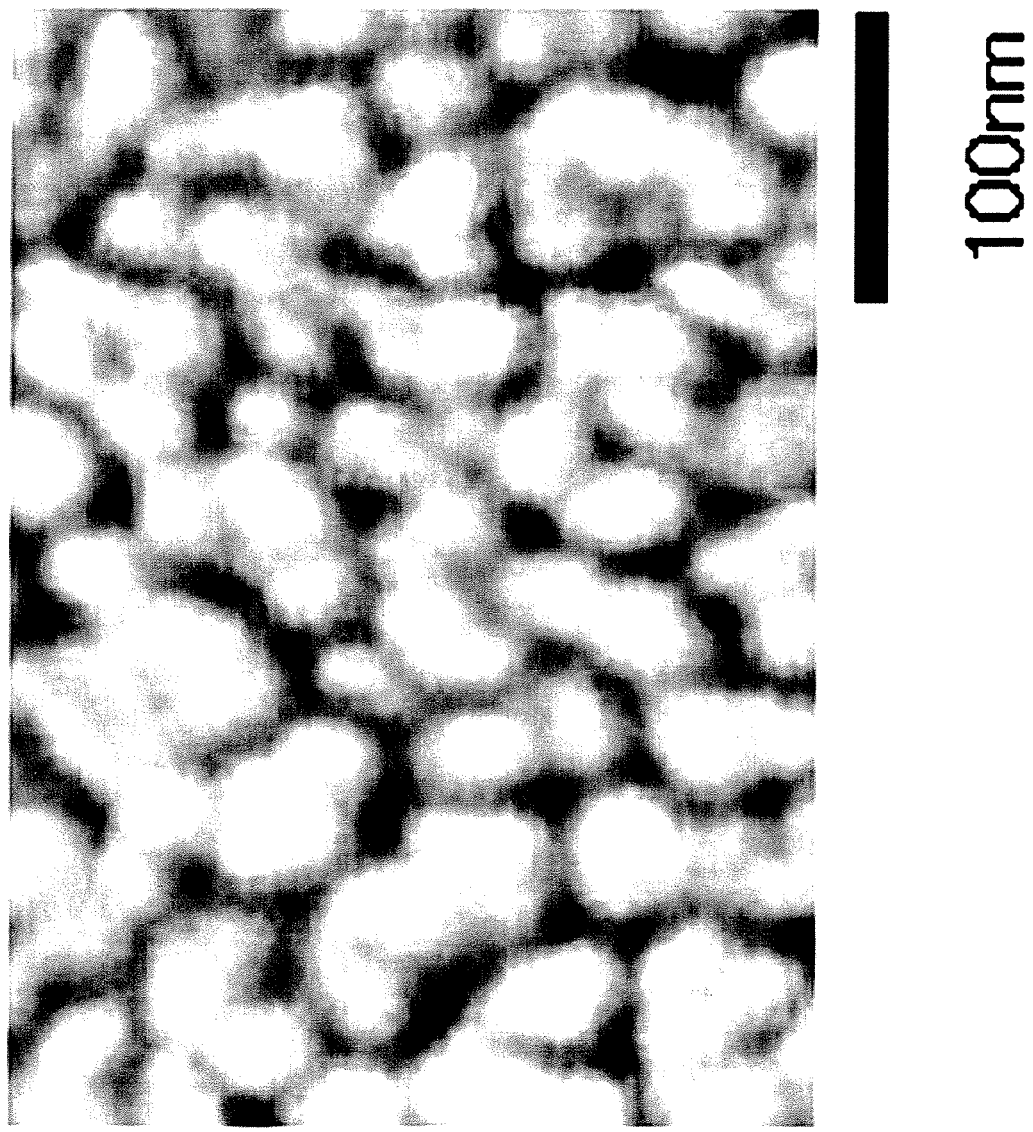
FIG. 29 is a SEM surface image of Sample No. 15.
Figure 30:
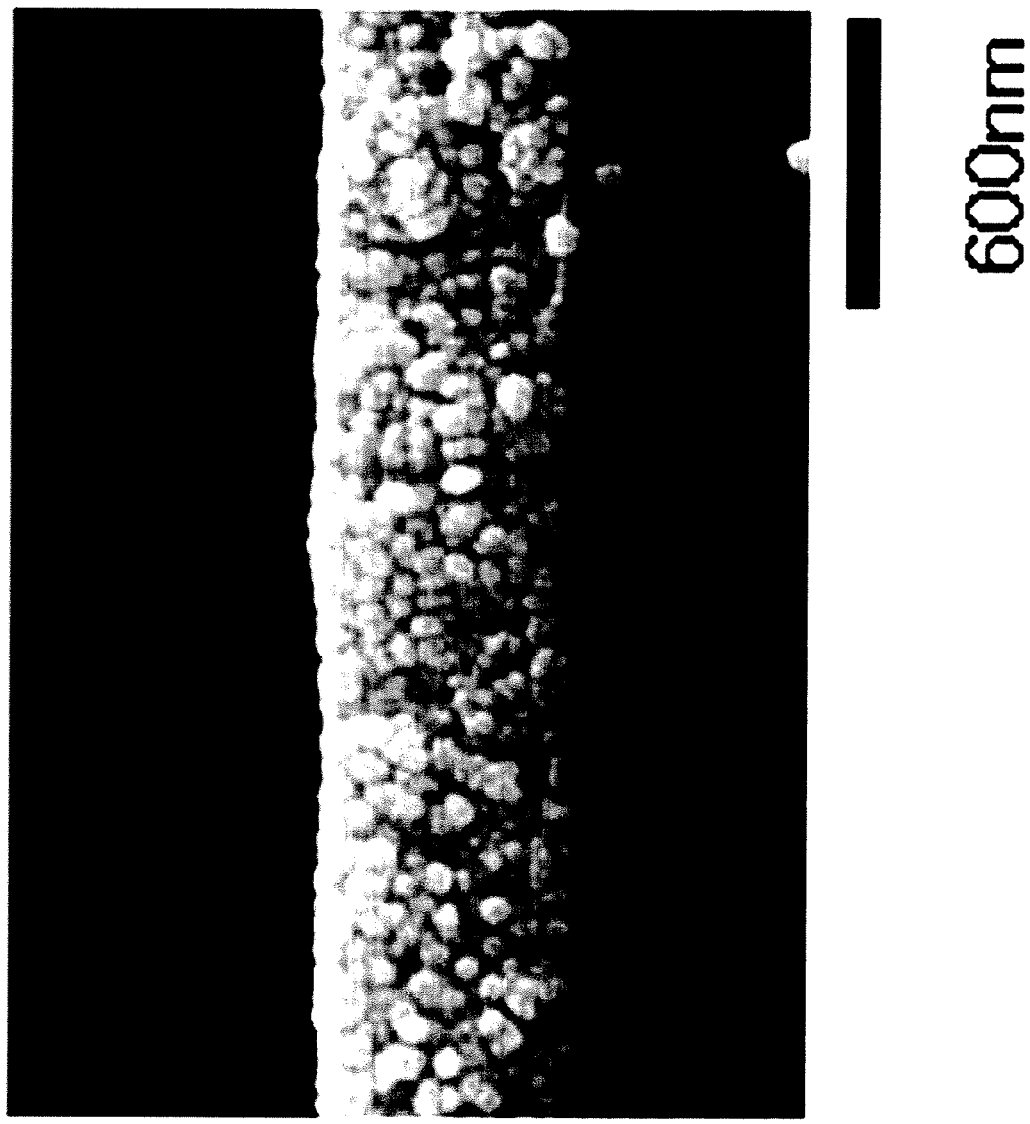
FIG. 30 is a SEM sectional image of Sample No. 15.

FIG. 21 and FIG. 22 respectively show the SEM surface image and the SEM sectional image of Sample No. 11; FIG. 23 and FIG. 24 respectively show the SEM surface image and the SEM sectional image of Sample No. 12; FIG. 25 and FIG. 26 respectively show the SEM surface image and the SEM sectional image of Sample No. 13; FIG. 27 and FIG. 28 respectively show the SEM surface image and the SEM sectional image of Sample No. 14; and FIG. 29 and FIG. 30 respectively show the SEM surface image and the SEM sectional image of Sample No. 15.

As is clear from FIG. 21 to FIG. 30, it was confirmed that ultrafine ZnO particles were formed into a film at a high density without being influenced by the heat treatment temperature and that no cracks were formed.

Moreover, Sample No. 11 (heat treatment temperature: 250° C.) and Sample No. 15 (heat treatment temperature: 700° C.) were observed also by TEM.

Figure 31:
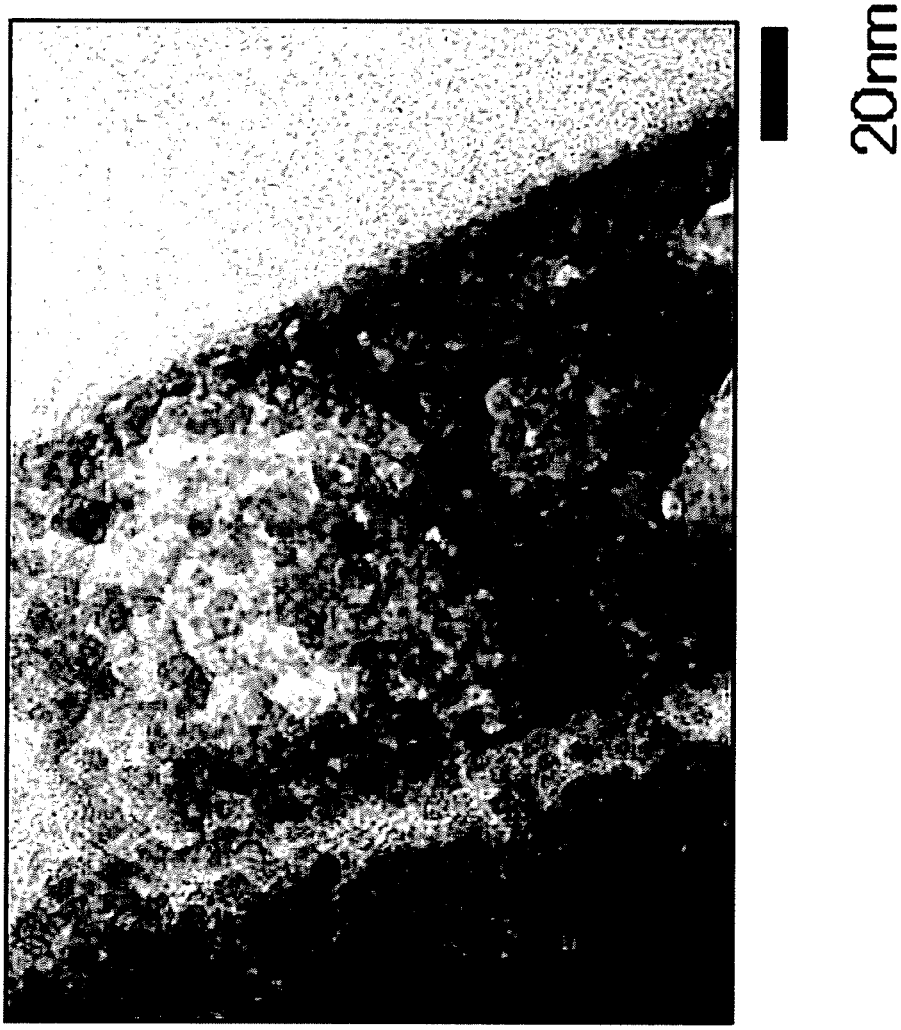
FIG. 31 is a TEM image of Sample No. 11.
Figure 32:
FIG. 32 is a TEM image of Sample No. 15.

FIG. 31 shows the TEM image of Sample No. 11, and FIG. 32 shows the TEM image of Sample No. 15.

In the TEM image of FIG. 31, the average particle diameter $D_{50}$ of ultrafine ZnO particles was as small as about 7 nm, whereas in FIG. 32, the average particle diameter $D_{50}$ of ultrafine ZnO particles was as large as about 30 nm. Namely, it was found that the particle diameter could be easily controlled only by performing heat treatment at different temperatures even in using the same ZnO dispersion.

The invention claimed is:

1. An ultrafine zinc oxide particle dispersion comprising: a hydrophobic solvent; and
a plurality of ultrafine zinc oxide particles having an average particle diameter $D_{50}$ of 10 nm or less and a ratio of a standard deviation σ to the average particle diameter $D_{50}$, $\sigma/D_{50}$, of 0.2 or less in a monodispersed state in the hydrophobic solvent,
wherein individual particles of the plurality of ultrafine zinc oxide particles are surrounded by both a primary surfactant that extends from a surface of the individual particles by a first distance and a secondary surfactant that extends from the surface of the individual particles by a second distance, the first distance being greater than the second distance,
wherein the hydrophobic solvent is selected from the group consisting of nonpolar hydrocarbons, ethers and petroleum hydrocarbons, and the primary surfactant is a polyoxyethylene nonylphenyl ether represented by:

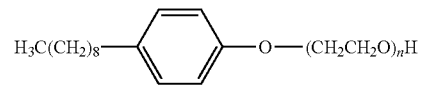

wherein n is an integer in a range of 1 to 20.

2. The ultrafine zinc oxide particle dispersion according to claim 1, wherein the ultrafine zinc oxide particles have an average particle diameter $D_{50}$ of 5 nm or less.

3. The ultrafine zinc oxide particle dispersion according to claim 2, wherein the secondary surfactant comprises a 4 to 10 carbon atom alcohol.

4. The ultrafine zinc oxide particle dispersion according to claim 3 wherein the alcohol is an alkanol.

5. The ultrafine zinc oxide particle dispersion according to claim 4, further comprising an aminoalcohol.

6. The ultrafine zinc oxide particle dispersion according to claim 3, further comprising an aminoalcohol.

7. The ultrafine zinc oxide particle dispersion according to claim 2, wherein the secondary surfactant is an alkanol.

8. The ultrafine zinc oxide particle dispersion according to claim 1, further comprising an aminoalcohol.

9. A method for producing an ultrafine zinc oxide particle dispersion comprising:
providing a water-in-oil microemulsion comprising hydrophobic solvent, a primary surfactant, a secondary surfactant, and water, wherein the hydrophobic solvent is selected from the group consisting of nonpolar hydrocarbons, ethers and petroleum hydrocarbons, and the primary surfactant is a polyoxyethylene nonylphenyl ether represented by:

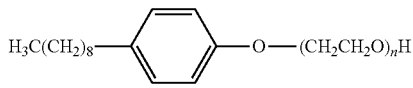

wherein n is an integer in a range of 1 to 20;
providing a zinc alkoxide solution comprising zinc alkoxide, aminoalcohol, and alcohol; and
combining the zinc alkoxide solution and the microemulsion under hydrolysis reaction conditions to produce a plurality of ultrafine zinc oxide particles having an average particle diameter $D_{50}$ of 10 nm or less and a ratio of a standard deviation $\sigma$ and the average particle diameter $D_{50}$, $\sigma/D_{50}$, of 0.2 or less in a monodispersed state in the hydrophobic solvent,
wherein individual particles of the plurality of ultrafine zinc oxide particles are surrounded by both the primary surfactant and the secondary surfactant, and the primary surfactant extends from a surface of the individual particles by a first distance and the secondary surfactant that extends from the surface of the individual particles by a second distance, the first distance being greater than the second distance.

10. The method for producing an ultrafine zinc oxide particle dispersion according to claim 9, wherein a molar amount of the aminoalcohol is at least the same molar amount as the zinc alkoxide.

11. The method for producing an ultrafine zinc oxide particle dispersion according to claim 10, wherein the zinc alkoxide is diethoxy zinc, the aminoalcohol is monoethanolamine, and the alcohol is ethanol.

12. The method for producing an ultrafine zinc oxide particle dispersion according to claim 11, wherein the secondary surfactant is a 4 to 10 carbon atom alcohol.

13. The method for producing an ultrafine zinc oxide particle dispersion according to claim 12, wherein the alcohol is an alkanol.

14. The method for producing an ultrafine zinc oxide particle dispersion according to claim 12, further comprising heating the ultrafine zinc oxide dispersion to form a zinc oxide film, wherein a ratio of a maximum emission intensity P1 in a visible range to a maximum emission intensity P2 in an ultraviolet range of the zinc oxide film, P1/P2, is 0.2 or less.

15. The method for producing an ultrafine zinc oxide particle dispersion according to claim 12, further comprising applying the ultrafine zinc oxide particle dispersion to a substrate and subjecting the substrate having the ultrafine zinc oxide particle dispersion thereon to heat.

* * * * *